United States Patent
Davidson et al.

(10) Patent No.: US 12,221,635 B2
(45) Date of Patent: Feb. 11, 2025

(54) SULFAMIDASE (SGSH) VARIANTS, VECTORS, COMPOSITIONS AND METHODS AND USES FOR TREATING MUCOPOLYSACCHARIDOSIS TYPE IIIA (MPS IIIA)

(71) Applicant: The Children's Hospital of Philadelphia, Philadelphia, PA (US)

(72) Inventors: Beverly L. Davidson, Philadelphia, PA (US); Yonghong Chen, Philadelphia, PA (US)

(73) Assignee: The Childeren's Hospital of Philadelphia, Philadelphia, PA (US)

( * ) Notice: Subject to any disclaimer, the term of this patent is extended or adjusted under 35 U.S.C. 154(b) by 926 days.

(21) Appl. No.: 16/611,458

(22) PCT Filed: May 11, 2018

(86) PCT No.: PCT/US2018/032454
§ 371 (c)(1),
(2) Date: Nov. 6, 2019

(87) PCT Pub. No.: WO2018/209317
PCT Pub. Date: Nov. 15, 2018

(65) Prior Publication Data
US 2021/0324354 A1    Oct. 21, 2021

Related U.S. Application Data

(60) Provisional application No. 62/505,423, filed on May 12, 2017.

(51) Int. Cl.
| | | |
|---|---|---|
| *C12N 15/63* | (2006.01) | |
| *A61K 45/06* | (2006.01) | |
| *A61K 48/00* | (2006.01) | |
| *A61P 25/00* | (2006.01) | |
| *C12N 7/00* | (2006.01) | |
| *C12N 9/14* | (2006.01) | |
| *C12N 15/86* | (2006.01) | |
| *A61K 38/00* | (2006.01) | |

(52) U.S. Cl.
CPC .............. *C12N 9/14* (2013.01); *A61K 45/06* (2013.01); *A61K 48/005* (2013.01); *A61K 48/0075* (2013.01); *A61K 48/0083* (2013.01); *A61P 25/00* (2018.01); *C12N 7/00* (2013.01); *C12N 15/86* (2013.01); *A61K 38/00* (2013.01); *C12Y 310/01001* (2013.01)

(58) Field of Classification Search
CPC .... A61K 48/005; A61K 48/0075; C12N 9/14; C12N 15/86; C12N 15/8645; C12N 15/63; C12N 2750/14143; C07H 21/04; C12Y 310/01001
See application file for complete search history.

(56) References Cited

U.S. PATENT DOCUMENTS

| | | | | |
|---|---|---|---|---|
| 5,972,333 A | * | 10/1999 | Scott ........................ | A61P 3/00 |
| | | | | 424/94.6 |
| 9,279,132 B2 | * | 3/2016 | Bosch Tubert ......... | A61P 19/00 |
| 9,849,195 B2 | | 12/2017 | Davidson | |

FOREIGN PATENT DOCUMENTS

| | | | | |
|---|---|---|---|---|
| JP | 2013-531490 A | 8/2013 | | |
| WO | WO-2011119773 A1 | * 9/2011 | ......... | A61K 38/1866 |
| WO | 2011-154520 A1 | 12/2011 | | |
| WO | 2016/007909 A2 | 1/2016 | | |

OTHER PUBLICATIONS

Sorentino (EMBO Mol Med, 5: 675-690, 2013) (Year: 3013).*
Haurigot (The Journal of Clinical Inventigtion, 123(8): 1-19, 2013). (Year: 2013).*
Ruzo (Mol Ther, 16: 1-389, 2008). (Year: 2008).*
Kotterman et al., 2014 (Nature Reviews, vol. 15, p. 445-451).*
Shim et al., 2017 (Current Gene Therapy, vol. 17, No. 5, p. 1-18).*
Lenzi et al., 2014 (NCBI Bookshelf, A Service of the National Library of Medicine, National Institute of Health, Oversight and Review of Clinical Gene Transfer Protocols: Assessing the Role of the Recombinant DNA Advisory Committee. Washington (DC): National Academies Press (US), pp. 1-16).*
Bryan et al., 2013 (http://www.elsevierblogs.com/currentcomments/?p=962, Implications of protein fold switching, p. 1-4).*
Maqbool et al., 2015 (Biochemical Society Transactions, vol. 43, No. 5, p. 1011-1017).*
Cruz et al., 2017 (Methods in Molecular Biology, vol. 1654, Chapter 5, pp. 55-75).*
Nagpal et al., 2022 (Indian Journal of Ophthalmology, vol. 70, No. 7, pp. 2249-2261).*
Chen, Y., et al., Overcoming Limitations Inherent in Sulfamidase to Improve MPS IIIA Gene Therapy, Molecular Therapy, May 1, 2017, 25(5), Suppl. 1:243.
Anson, D.S., et al., Lentiviral-mediated gene correction of mucopolysaccharidosis type IIIA, Genetic Vaccines and Therapy, Jan. 16, 2007, 5(1):1-8.
Oslpova, L.A., et al., Sanfilippo Syndrome, Vestnik Rossiiskoi Akademii Meditsinskikh Nauk=Annals of the Russian Academy of Medical Sciences. 2015; 70 (4):419-427. Doi: 10.15690/vramn.v70.i4.1407) (English Abstract; bottom of p. 1).

(Continued)

*Primary Examiner* — Shin Lin Chen
(74) *Attorney, Agent, or Firm* — Pillsbury Winthrop Shaw Pittman LLP; Robert M. Bedgood

(57) ABSTRACT

The invention relates to sulfamidase (SGSH) and SGSH variants. SGSH and SGSH variants can be delivered by way of a recombinant adeno-associated virus (rAAV) particle to a mammal's central nervous system (CNS) to transduce CNS cells that contact cerebrospinal fluid (CSF). Target mammals for SGSH and SGSH variant administration include mammals with a deficiency or defect in SGSH expression or function.

54 Claims, 21 Drawing Sheets
Specification includes a Sequence Listing.

(56) References Cited

OTHER PUBLICATIONS

Chen, Y., et al., Overcoming Limitations Inherent in Sulfamidase to Improve Mucopolysaccharidosis IIIA Gene Therapy, Molecular Therapy, Jan. 31, 2018, 26(4):1118-1126.
Fraldi, A., et al., Functional correction of CNS lesions in an MPS-IIIA mouse model by intracerebral MV-mediated delivery of sulfamidase and SUMF1 genes, Human Molecular Genetics, Nov. 15, 2007, 16(22):2693-2702.
Haurigot, V., et al., Whole body correction of mucopolysaccharidosis IIIA by intracerebrospinal fluid gene therapy, The Journal of Clinical Investigation, Jul. 1, 2013, 123(8):3254-3271.
Ruzo, A., et al., Correction of Pathological Accumulation of Glycosaminoglycans in Central Nervous System and Peripheral Tissues of MPSIIIA Mice Through Systemic AAV9 Gene Transfer, Human Gene Therapy, Oct. 17, 2012, 23:1237-1246.
Broun, P., et al., Catalytic Plasticity of Fatty Acid Modification Enzymes Underlying Chemical Diversity of Plant Lipids, Science, Nov. 13, 1998, 282:1315-1317.
Sidhu, N.S., et al. Structure of sulfamidase provides insight into the molecular pathology of mucopolysaccharidosis IIIA, Acta Crystallogr. Section D: Biol. Crystallogr. Feb. 5, 2014, D70(Pt 5):1321-1335. doi: 10.1107/S1399004714002739.
Whisstock, J.C., et al. Prediction of protein function from protein sequence and structure, Quarterly Reviews of Biophysics, 36 3 (2003):307-340. DOI: 10.1017/S0033583503003901.
Yampolsky, L.Y., et al., The Exchangeability of Amino Acids in Proteins, Genetics, May 11, 2005, 170:1459-1472. DOI: 10.1534/genetics.104.039107.

\* cited by examiner

FIG. 4A

| Variants | SGSHv1 | SGSHv2 | SGSHv3 | SGSHv4 | SGSHv5 |
|---|---|---|---|---|---|
| AA changes | N41Q | N142Q | N151Q | N264Q | N413Q |

FIG. 4B

SULFAMIDASE (SGSH) VARIANTS, VECTORS, COMPOSITIONS AND METHODS AND USES FOR TREATING MUCOPOLYSACCHARIDOSIS TYPE IIIA (MPS IIIA)

RELATED APPLICATION INFORMATION

This patent application is the National Phase of International Application No. PCT/US2018/032454, filed May 11, 2018, which designated the U.S. and that International Application was published under PCT Article 21 (2) in English, which claims the benefit of, and priority to, U.S. Provisional patent application No. 62/505,423, filed May 12, 2017. The entire contents of the foregoing applications are expressly incorporated herein by reference in their entirety, including all text, tables, sequence listings and drawings.

SEQUENCE LISTING

The instant application contains a Sequence Listing which has been submitted electronically in ASCII format and is hereby incorporated by reference in its entirety. Said ASCII copy, created on Nov. 6, 2019, is named "CHOP0508339_ST25.txt" and is 7.49 KB in size.

INTRODUCTION

Mucopolysaccharidosis type IIIA (MPS IIIA) is a lysosomal storage disease caused by the deficiency of sulfamidase. MPS IIIA, caused by mutations in sulfamidase (SGSH), is characterized by progressive neurodegeneration accompanied by loss of social skills and aggressive behavior, hyperactivity and sleep disturbance. Somatic features are often mild and variable. To correct the brain pathology in lysosomal storage diseases, our group and others have successfully introduced genes encoding the missing enzymes into brain. The basis of this gene therapy method lies in the efficient secretion of lysosomal enzymes. After the enzyme is effectively secreted from gene corrected cells, then it could potentially be taken up by nearby cells, resulting in cross-correction.

SUMMARY

As disclosed herein, a modified sulfamidase (SGSH) has improved secretion and uptake, to provide greater therapeutic benefit for MPS IIIA treatment. The effects of mutating five different mannose-6-phosphorylation (M6P) sites on SGSH were evaluated. The efficiency of secretion was variable, and the modifications affected secretion from transduced or transfected cells. One particular M6P site modification, N264Q, resulted in elevated levels of SGSH secretion.

Further studies showed that SGSH M6P site modification afforded several additional valuable attributes. First, the modification not only increased enzyme secretion, but also decreased enzyme buildup in the cells, which, if there was buildup, could impart secondary lysosomal dysfunction. Second, this SGSH variant was processed correctly in the cells and matured to the active form in the lysosome. Third, surprisingly this SGSH variant appears to be more efficiently taken up by cells, possibly by using a receptor different than that used for the normal, unmodified SGSH. As a result, this modified SGSH is expected to be superior to the wild type SGSH in gene therapy or enzyme replacement therapy for MPS IIIA patients. In MPS IIIA animal model studies disclosed herein, this modified SGSH was superior to the wild type SGSH in terms of providing a cognitive benefit and/or a reduction in cognitive deficits in the MPS IIIA animals, presumably owing to or more of the attributes.

In accordance with the invention, methods of delivering sulfamidase (SGSH) to the central nervous system of a mammal are provided. In one embodiment, a method includes administering to the mammal's central nervous system (CNS) a recombinant adeno-associated virus (rAAV) particle comprising a nucleic acid encoding sulfamidase (SGSH) variant effective to transduce cells that contact the cerebrospinal fluid (CSF) of the mammal such that the cells express and secrete the sulfamidase (SGSH) variant in the mammal.

In accordance with the invention, methods of treating a disease in a mammal caused by a deficiency or defect in sulfamidase (SGSH) expression or function are provided. In one embodiment, a method includes administering to the central nervous system (CNS) of the mammal a recombinant adeno-associated virus (rAAV) particle comprising a nucleic acid encoding a sulfamidase (SGSH) variant in a manner effective to transduce cells that contact the CNS of the mammal, wherein the cell expresses and secretes the sulfamidase (SGSH) variant so as to treat the disease.

In accordance with the invention, methods of delivering sulfamidase (SGSH) to the central nervous system of a mammal are provided. In one embodiment, a method includes administering to the mammal's brain parenchyma, subarachnoid space and/or intrathecal space a recombinant adeno-associated virus (rAAV) particle comprising a nucleic acid encoding a sulfamidase (SGSH) variant in a manner effective to transduce brain parenchyma cells or cells that contact the cerebrospinal fluid (CSF) of the mammal such that the cells express and secrete the SGSH variant in the mammal.

In accordance with the invention, methods of treating a disease in a mammal caused by a deficiency or defect in sulfamidase (SGSH) expression or function are provided. In one embodiment, a method includes administering to the mammal's brain parenchyma, subarachnoid space and/or intrathecal space a recombinant adeno-associated virus (rAAV) particle comprising a nucleic acid encoding a sulfamidase (SGSH) variant inserted between a pair of AAV inverted terminal repeats in a manner effective to transduce brain parenchyma cells or cells that contact the cerebrospinal fluid (CSF) of the mammal, wherein the cell expresses and secretes the SGSH variant, so as to treat the disease.

In the invention methods, administration or delivery can be to the brain ventricle. In the invention methods, administration or delivery of the rAAV particle can be to the mammal's brain ventricle, subarachnoid space and/or intrathecal space. In invention methods, administration or delivery can be to a lateral brain ventricle. In invention methods administration or delivery can be to ependymal cells, pial cells, endothelial cells, brain ventricle cells, meningeal cells, glial cells and/or neurons.

In the invention methods, cells to which the rAAV is administered or delivered secrete the SGSH variant into the CNS of said mammal. In the invention methods, cells to which the rAAV is administered or delivered secrete the SGSH variant into the CSF of said mammal.

In the invention methods, ependymal cells, pial, endothelial, brain ventricle, meningeal, glial cell and/or neuron expresses the SGSH variant and/or ependymal, pial, endothelial, brain ventricle, meningeal cell, glial cell and/or neuron secretes the SGSH variant into the CSF.

In the invention methods, a rAAV particle or particles include an AAV capsid protein and a vector genome in which the nucleic acid encoding a sulfamidase (SGSH) variant is inserted between a pair of AAV inverted terminal repeats (ITRs).

In the invention methods, the AAV capsid protein can be derived from or selected from the group consisting of AAV1, AAV2, AAV3, AAV4, AAV5, AAV6, AAV7, AAV8, AAV9, AAV10, AAV11, AAV12, AAV-rh74, AAV-rh10 and AAV-2i8 VP1, VP2 and/or VP3 capsid proteins, or a capsid sequence having 70% or more identity to AAV1, AAV2, AAV3, AAV4, AAV5, AAV6, AAV7, AAV8, AAV9, AAV10, AAV11, AAV12, AAV-rh74, AAV-Rh10, or AAV-2i8 VP1, VP2 and/or VP3 capsid sequences.

In the invention methods, one or more of the pair of AAV ITRs can be derived from, comprises or consists of an AAV1, AAV2, AAV3, AAV4, AAV5, AAV6, AAV7, AAV8, AAV9, AAV10, AAV11, AAV12, AAV-rh74, AAV-rh10 or AAV-2i8 ITR, or an ITR having 70% or more identity to AAV1, AAV2, AAV3, AAV4, AAV5, AAV6, AAV7, AAV8, AAV9, AAV10, AAV11, AAV12, AAV-rh74, AAV-Rh10, or AAV-2i8 ITR sequence.

In the invention methods, the nucleic acid encoding a sulfamidase (SGSH) variant further includes an expression control element modulating the expression of the nucleic acid. In certain embodiments, an expression control element comprises a promoter. In certain embodiments, an expression control element comprises an enhancer element.

In particular embodiments, an expression control element comprises a CMV enhancer, chicken beta actin promoter, CAG promoter and/or a sequence having 80% or more identity to CMV enhancer set forth in SEQ ID NO:2 and/or a sequence having 80% or more identity to CAG promoter set forth in SEQ ID NO:3.

In the invention methods, the nucleic acid can further include one or more of an intron, a filler polynucleotide sequence and/or poly A signal, or a combination thereof.

In certain embodiments, a plurality of rAAV particles are administered or delivered to the subject.

In certain embodiments, rAAV particles are administered at a dose of about $1\times10^6$ to about $1\times10^{18}$ vg/kg.

In certain embodiments, rAAV particles are administered at a dose from about $1\times10^7$-$1\times10^{17}$, about $1\times10^8$-$1\times10^{16}$, about $1\times10^9$-$1\times10^{15}$, about $1\times10^{10}$-$1\times10^{14}$, about $1\times10^{10}$-$1\times10^{13}$, about $1\times10^{10}$-$1\times10^{13}$, about $1\times10^{10}$-$1\times10^{11}$, about $1\times10^{11}$-$1\times10^{12}$, about $1\times10^{12}$-$1\times10^{13}$, or about $1\times10^{13}$-$1\times10^{14}$ vector genomes per kilogram (vg/kg) of the mammal.

In certain embodiments, rAAV particles are administered at a dose of about 0.5-4 ml of $1\times10^6$-$1\times10^{16}$ vg/ml.

In certain embodiments, a method of the invention further includes administering a plurality of AAV empty capsids. In certain embodiments, rAAV particles are formulated with AAV empty capsids for administration.

In certain embodiments, AAV empty capsids are administered or formulated with 1.0 to 100-fold excess of rAAV vector particles. In certain embodiments, AAV empty capsids are administered or formulated with about 1.0 to 100-fold excess of AAV empty capsids to rAAV particles.

In certain embodiments, the rAAV particles formulated with AAV empty capsids is appropriate for administration or delivery to a mammal.

In certain embodiments, the AAV empty capsids are formulated for administration or delivery to a mammal.

In certain embodiments, the delivering or administering comprises intraventricular injection and/or intraparenchymal injection.

In certain embodiments, rAAV particle is injected at a single location in the brain. In certain embodiments, rAAV particle is injected at 1-5 locations in the brain.

In certain embodiments, rAAV particle is administered to the: rostral lateral ventricle; and/or caudal lateral ventricle; and/or right lateral ventricle; and/or left lateral ventricle; and/or right rostral lateral ventricle; and/or left rostral lateral ventricle; and/or right caudal lateral ventricle; and/or left caudal lateral ventricle.

In certain embodiments, rAAV particle is administered in single or multiple doses to any of the mammal's cisterna magna, intraventricular space, brain ventricle, subarachnoid space, intrathecal space and/or ependyma.

In certain embodiments, a method provides increased SGSH variant expression or SGSH function to the CNS. In certain embodiments, a method increases SGSH variant expression to between about 5-50% of normal SGSH expression. In certain embodiments, a method increases SGSH variant expression to above 50% of normal SGSH expression.

In certain embodiments, a method inhibits, decreases, or reduces cognitive deficits or defects due to a defect or deficiency of endogenous SGSH in said mammal.

In certain embodiments, a method increases, improves, preserves, restores or rescues cognitive function loss or spatial learning loss due to a defect or deficiency of endogenous SGSH in said mammal.

In certain embodiments, a method increases, improves, preserves, restores or rescues memory deficits or defects of the mammal.

In certain embodiments, a method increases, preserves, restores or rescues neuron function, or viability.

In certain embodiments, a method increases, preserves, restores or rescues cortical neuron function, or viability.

In certain embodiments, a method increases, preserves, restores or rescues cortical motor neuron function, or viability.

In certain embodiments, a method inhibits, decreases, or prevents neuron degeneration or death.

In certain embodiments, a method inhibits, decreases, or prevents cortical neuron degeneration or death.

In certain embodiments, a method inhibits, decreases, or prevents cortical motor neuron degeneration or death.

In certain embodiments, a method improves, reduces or decreases a symptom or adverse effect of SGSH defect or deficiency.

In certain embodiments, a method stabilizes, prevents worsening or reverses a symptom or adverse effect of SGSH defect or deficiency.

In certain embodiments, a symptom or adverse effect is an early stage or late stage symptom; a behavior, personality or language symptom; a motor function symptom; and/or a cognitive symptom.

In certain embodiments, a method provides greater SGSH variant secretion by transduced cells compared to secretion of the non-variant SGSH set forth as SEQ ID NO:1.

In certain embodiments, a method provides greater uptake of the SGSH variant by non-transduced cells compared to uptake of non-variant SGSH set forth as SEQ ID NO:1.

In certain embodiments, a method inhibits or decreases secondary enzyme (e.g., beta glucuronidase) production or accumulation in cells.

Invention subjects including mammals. In one embodiment, a mammal is a non-rodent mammal. In another embodiment, a mammal is a primate, horse, sheep, goat, pig, or dog. In another embodiment, a mammal is a primate.

In another embodiment, a primate is human. In one aspect, a human is a child. In a particular aspect, a child is from about 1 to about 8 years of age.

Invention subjects include mammals, such as primates and humans that exhibit a loss of or reduced endogenous SGSH expression or function.

Invention subjects include mammals, such as primates and humans that are homozygous (Sgsh$^{-/-}$) or heterozygous (Sgsh$^{+/-}$) with respect to lost or reduced SGSH expression or function.

Invention methods include treatment of any disease or disorder caused by or associated with a deficiency or defect in SGSH expression or function.

In certain embodiments, a method includes administering one or more immunosuppressive agents. In particular embodiments, and immunosuppressive agent is administered prior to or contemporaneously with administration or delivery of said rAAV particle.

In certain embodiments, an immunosuppressive agent is an anti-inflammatory agent.

In certain embodiments, an SGSH variant is mammalian. In particular aspects, an SGSH variant is a primate, horse, sheep, goat, pig, or dog SGSH.

In certain embodiments, an SGSH variant is human.

In certain embodiments, an SGSH variant exhibits greater secretion by transduced cells compared to non-variant SGSH set forth as SEQ ID NO:1.

In certain embodiments, an SGSH variant exhibits increased uptake by cells compared to uptake of non-variant SGSH set forth as SEQ ID NO:1.

In certain embodiments, SGSH variant uptake by cells does not require mannose-6-phosphate receptor.

In certain embodiments, an SGSH variant is distributed to non-transduced cells in CNS.

In certain embodiments, an SGSH variant is distributed to non-transduced CNS cells by way of cerebrospinal fluid (CSF).

In certain embodiments, an SGSH variant is distributed to non-transduced CNS cells located distal to the transduced cells.

In certain embodiments, an SGSH is taken up by said CNS cells.

In certain embodiments, an SGSH variant is at least 90% identical to SEQ ID NO:1.

In certain embodiments, an SGSH variant comprises a variant of SEQ ID NO:1.

In certain embodiments, an SGSH variant is at least 90% identical to SEQ ID NO:1 having an amino acid substitution at position 264.

In certain embodiments, an SGSH variant is at least 90% identical to SEQ ID NO:1 having an asparagine (N)→glutamine (Q) substitution at position 264.

In certain embodiments, an SGSH variant comprises SEQ ID NO:1 having an amino acid substitution at position 264.

In certain embodiments, an SGSH variant comprises SEQ ID NO:1 having an asparagine (N)→glutamine (Q) substitution at position 264.

DESCRIPTION OF DRAWINGS

FIG. 4A shows list of modifications of SGSH M6P.

FIG. 4B shows that M6P site modification of SGSH improves secretion.

DETAILED DESCRIPTION

Figure 1:
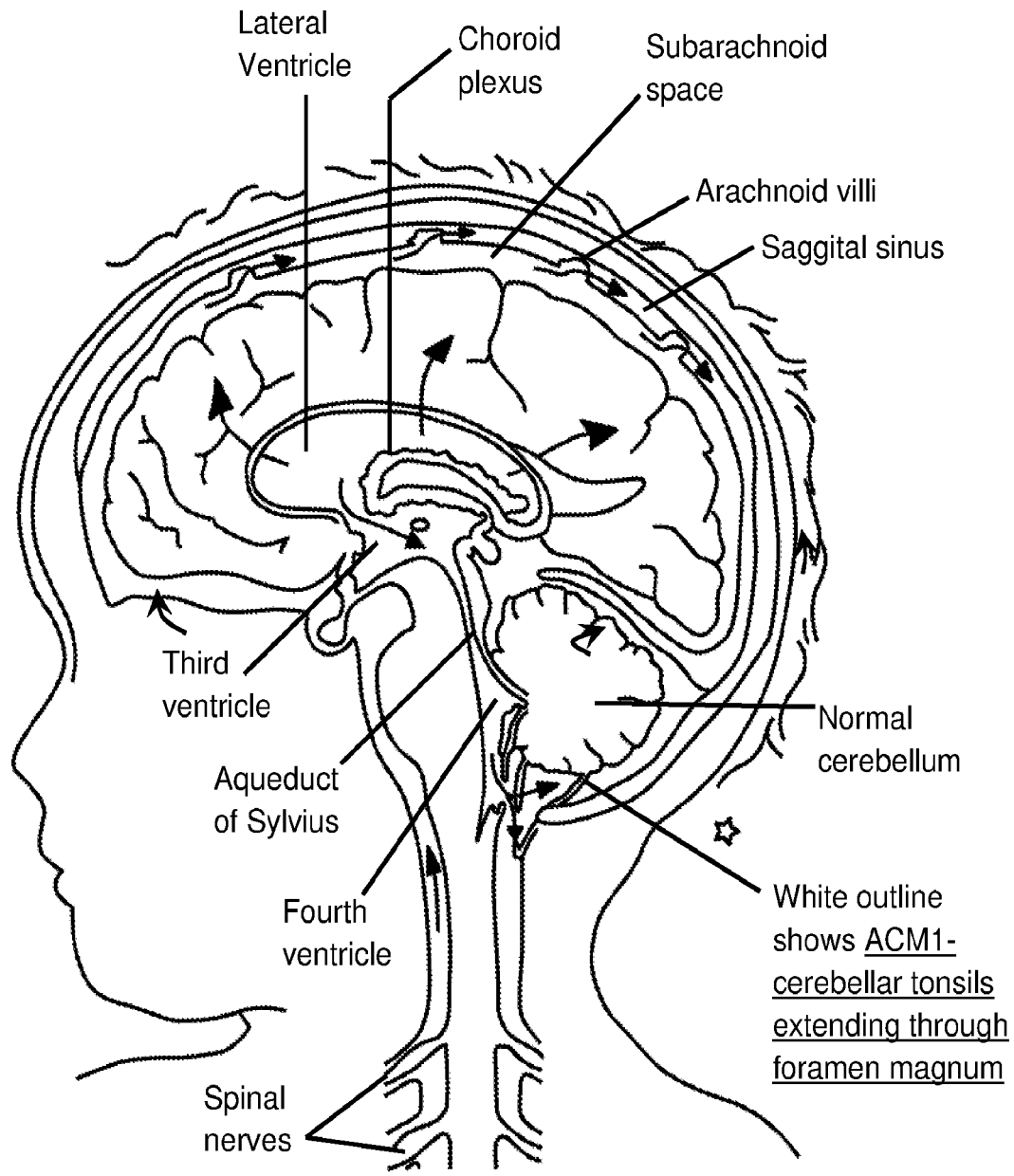
FIG. 1 shows AAV delivery approaches for LSD therapy. Injection into brain parenchyma and cerebrospinal fluid (CSF). For some serotypes, effective transduction of ependyma for CSF distribution to underlying neural cells.

Provided herein are methods and uses for administering to a mammal, in need of a method described herein, that would benefit from increased SGSH activity or expression, e.g., in a subject that exhibits a loss of or reduced endogenous SGSH expression or function. Thus, in one embodiment, SGSH activity or expression is reduced compared to normal SGSH or SGSH is absent in a mammal. In a particular embodiment, a mammal in need of SGSH has or is at risk of having MPS IIIA.

In certain embodiments, provided herein are methods of treating a disease in mammal caused by a deficiency or defect in SGSH activity or expression by administering, directly to a tissue or fluid of the central nervous system, a vector, such as rAAV particles that direct the expression of protein having SGSH activity (referred to herein as rAAV-SGSH particles), optionally the SGSH variant exhibiting greater than wild-type secretion by vector transduced cells and/or greater than wild-type SGSH uptake by non-transduced cells. Disclosed herein are data showing rAAV-SGSH delivery/administration to the brain and/or spinal cord in an animal model is effective to provide expression of SGSH, secretion of SGSH from transduced cells, and broad distribution of SGSH in various regions of the brain/CNS and uptake by cells.

In additional embodiments, a method or use described herein is used to treat, prevent, inhibit, reduce, decrease or delay the number, severity, frequency, progression or onset of one or more symptoms of SGSH deficiency.

In certain embodiments, rAAV-SGSH particles are administered to the brain. In certain embodiments, rAAV-SGSH particles are administered to the cerebral spinal fluid (CSF) of said mammal.

In certain embodiments, rAAV-SGSH particles are administered to the ventricular system. In certain embodiments, rAAV-SGSH particles are administered to the brain ventricle.

In certain embodiments, rAAV-SGSH particles are administered to the brain parenchyma, subarachnoid space and/or intrathecal. In certain embodiments, rAAV-SGSH particles are administered to the cisternae magna, intraventricular space, subarachnoid space, intrathecal space and/or ependyma of said mammal.

In still further embodiments, rAAV-SGSH particles are administered to the rostral lateral ventricle; and/or administered to the caudal lateral ventricle; and/or administered to the right lateral ventricle; and/or administered to the left lateral ventricle; and/or administered to the right rostral lateral ventricle; and/or administered to the left rostral lateral ventricle; and/or administered to the right caudal lateral ventricle; and/or administered to the left caudal lateral ventricle.

In still additional embodiments, rAAV-SGSH particles are administered such that the AAV particles contact and transduce CNS cells, such as ependymal cells of said mammal. Such transduced CNS cells (e.g., ependymal cells) express the encoded SGSH and the SGSH is secreted by the cells. In particular embodiments, the SGSH is expressed and/or in CSF, brain (e.g., striatum, thalamus, medulla, cerebellum, occipital cortex, frontal cortex and/or prefrontal cortex, spinal cord), and/or CNS. In particular embodiments, the SGSH is secreted into the CSF, brain (e.g., striatum, thalamus, medulla, cerebellum, occipital cortex, frontal cortex and/or prefrontal cortex, spinal cord), and/or CNS. In particular embodiments, the SGSH is secreted into the CSF, brain (e.g., striatum, thalamus, medulla, cerebellum, occipital cortex, frontal cortex and/or prefrontal cortex, spinal cord), and/or CNS, and is taken up by non-transduced CNS cells.

Any suitable mammal can be treated by a method or use described herein. Typically, a mammal is in need of a method described herein, that is suspected of having or that has a deficiency or defect in SGSH activity or expression.

Non-limiting examples of mammals include humans, non-human primates (e.g., apes, gibbons, chimpanzees, orangutans, monkeys, macaques, and the like), domestic animals (e.g., dogs and cats), farm animals (e.g., horses, cows, goats, sheep, pigs) and experimental animals (e.g., mouse, rat, rabbit, guinea pig). In certain embodiments a mammal is a human. In certain embodiments a mammal is a non-rodent mammal (e.g., human, pig, goat, sheep, horse, dog, or the like). In certain embodiments a non-rodent mammal is a human. A mammal can be any age or at any stage of development (e.g., an adult, teen, child, infant, or a mammal in utero). A mammal can be male or female. In certain embodiments a mammal can be an animal disease model, for example, animal models used for the study of a deficiency or defect in SGSH expression or function.

Mammals (subjects) treated by a method or composition described herein include adults (18 years or older) and children (less than 18 years of age). Children range in age from 1-2 years old, or from 2-4, 4-6, 6-18, 8-10, 10-12, 12-15 and 15-18 years old. Children also include infants. Infants typically range from 1-12 months of age.

In certain embodiments, a mammal is homozygous ($Sgsh^{-/-}$) with respect to lost or reduced SGSH expression or function. In certain embodiments, a mammal is heterozygous ($Sgsh^{+/-}$) with respect to lost or reduced SGSH expression or function.

Adeno associated virus (AAV) is a small nonpathogenic virus of the parvoviridae family. To date, numerous serologically distinct AAVs have been identified, and more than a dozen have been isolated from humans or primates. AAV is distinct from other members of this family by its dependence upon a helper virus for replication.

AAV genomes been shown to stably integrate into host cellular genomes; possess a broad host range; transduce both dividing and non-dividing cells in vitro and in vivo and maintain high levels of expression of the transduced genes. AAV viral particles are heat stable, resistant to solvents, detergents, changes in pH, temperature, and can be column purified and/or concentrated on CsCl gradients or by other means. The AAV genome comprises a single-stranded deoxyribonucleic acid (ssDNA), either positive- or negative-sensed. In the absence of a helper virus, AAV may integrate in a locus specific manner, for example into the q arm of chromosome 19. The approximately 5 kb genome of AAV consists of one segment of single stranded DNA of either plus or minus polarity. The ends of the genome are short inverted terminal repeats (ITRs) which can fold into hairpin structures and serve as the origin of viral DNA replication.

An AAV "genome" refers to a recombinant nucleic acid sequence that is ultimately packaged or encapsulated to form an AAV particle. An AAV particle often comprises an AAV genome packaged with capsid proteins. In cases where recombinant plasmids are used to construct or manufacture recombinant vectors, the vector genome does not include the portion of the "plasmid" that does not correspond to the vector genome sequence of the recombinant plasmid. This non vector genome portion of the recombinant plasmid is referred to as the "plasmid backbone," which is important for cloning and amplification of the plasmid, a process that is needed for propagation and recombinant virus production, but is not itself packaged or encapsulated into virus (e.g., AAV) particles. Thus, a vector "genome" refers to nucleic acid that is packaged or encapsulated by virus proteins and in the case of AAV, a capsid or capsid proteins.

The AAV virion (particle) is a non-enveloped, icosahedral particle approximately 25 nm in diameter. The AAV particle comprises an icosahedral symmetry comprised of three related capsid proteins, VP1, VP2 and VP3, which interact together to form the capsid. The right ORF often encodes the capsid proteins VP1, VP2, and VP3. These proteins are often found in a ratio of 1:1:10 respectively, but may be in varied ratios, and are all derived from the right-hand ORF. The VP1, VP2 and VP3 capsid proteins differ from each other by the use of alternative splicing and an unusual start codon. Deletion analysis has shown that removal or alteration of VP1 which is translated from an alternatively spliced message results in a reduced yield of infectious particles. Mutations within the VP3 coding region result in the failure to produce any single-stranded progeny DNA or infectious particles.

An AAV particle is a viral particle comprising an AAV capsid. In certain embodiments the genome of an AAV particle encodes one, two or all VP1, VP2 and VP3 polypeptides.

The genome of most native AAVs often contain two open reading frames (ORFs), sometimes referred to as a left ORF and a right ORF. The left ORF often encodes the non-structural Rep proteins, Rep 40, Rep 52, Rep 68 and Rep 78, which are involved in regulation of replication and transcription in addition to the production of single-stranded progeny genomes. Two of the Rep proteins have been associated with the preferential integration of AAV genomes into a region of the q arm of human chromosome 19. Rep68/78 have been shown to possess NTP binding activity as well as DNA and RNA helicase activities. Some Rep proteins possess a nuclear localization signal as well as several potential phosphorylation sites. In certain embodiments the genome of an AAV (e.g., an rAAV) encodes some or all of the Rep proteins. In certain embodiments the genome of an AAV (e.g., an rAAV) does not encode the Rep proteins. In certain embodiments one or more of the Rep proteins can be delivered in trans and are therefore not included in an AAV particle comprising a nucleic acid encoding a polypeptide.

The ends of the AAV genome comprise short inverted terminal repeats (ITR) which have the potential to fold into T-shaped hairpin structures that serve as the origin of viral DNA replication. Accordingly, the genome of an AAV comprises one or more (e.g., a pair of) ITR sequences that flank a single stranded viral DNA genome. The ITR sequences often have a length of about 145 bases each. Within the ITR region, two elements have been described which are believed to be central to the function of the ITR, a GAGC repeat motif and the terminal resolution site (trs). The repeat motif has been shown to bind Rep when the ITR is in either a linear or hairpin conformation. This binding is thought to position Rep68/78 for cleavage at the trs which occurs in a site- and strand-specific manner. In addition to their role in replication, these two elements appear to be central to viral integration. Contained within the chromosome 19 integration locus is a Rep binding site with an adjacent trs. These elements have been shown to be functional and necessary for locus specific integration.

In certain embodiments an AAV (e.g., a rAAV) comprises two ITRs. In certain embodiments an AAV (e.g., a rAAV) comprises a pair of ITRs. In certain embodiments an AAV (e.g., a rAAV) comprises a pair of ITRs that flank (i.e., are at each 5' and 3' end) of a polynucleotide that at least encodes a polypeptide having SGSH function or activity.

The term "vector" refers to small carrier nucleic acid molecule, a plasmid, virus (e.g., AAV vector), or other vehicle that can be manipulated by insertion or incorporation of a nucleic acid. Vectors such as AAV vectors can be used to introduce/transfer polynucleotides into cells, such that the polynucleotide therein is transcribed and subsequently translated by the cells.

An "expression vector" is a specialized vector that contains a gene or nucleic acid sequence with the necessary regulatory regions needed for expression in a host cell. A vector nucleic acid sequence generally contains at least an origin of replication for propagation in a cell and optionally additional elements, such as a heterologous polynucleotide sequence, expression control element (e.g., a promoter, enhancer), intron, ITR(s), polyadenylation signal.

A viral vector is derived from or based upon one or more nucleic acid elements that comprise a viral genome. Particular viral vectors include adeno-associated virus (AAV) vectors.

As disclosed herein, provided are vectors (e.g., AAV) comprising a nucleic acid sequence encoding a SGSH variant that exhibits greater secretion than wild-type SGSH when expressed by vector-transduced cells. As disclosed herein, also provided are vectors (e.g., AAV) comprising a nucleic acid sequence encoding a SGSH variant that exhibits greater uptake than wild-type SGSH (e.g., SEQ ID NO:1) by non-transduced cells. Also provided herein are vectors (e.g., AAV) comprising a nucleic acid sequence encoding a SGSH variant that exhibits greater secretion than wild-type SGSH (e.g., SEQ ID NO:1) when expressed by vector-transduced cells and that that exhibits greater uptake than wild-type SGSH (e.g., SEQ ID NO:1) by non-transduced cells.

The term "recombinant," as a modifier of vector, such as recombinant viral, e.g., lenti- or parvo-virus (e.g., AAV) vectors, as well as a modifier of sequences such as recombinant polynucleotides and polypeptides, means that the compositions have been manipulated (i.e., engineered) in a fashion that generally does not occur in nature. A particular example of a recombinant vector, such as an AAV vector would be where a polynucleotide that is not normally present in the wild-type viral (e.g., AAV) genome is inserted within the viral genome. An example of a recombinant polynucleotide would be where a nucleic acid (e.g., gene) encoding a SGSH polypeptide is cloned into a vector, with or without 5', 3' and/or intron regions that the gene is normally associated within the viral (e.g., AAV) genome. Although the term "recombinant" is not always used herein in reference to vectors, such as viral and AAV vectors, as well as sequences such as polynucleotides, "recombinant" forms including polynucleotides, nucleic acids, transgenes, etc. are expressly included in spite of any such omission.

A recombinant viral "vector" or recombinant "AAV vector" is derived from the wild type genome of a virus, such as AAV by using molecular methods to remove the wild type genome from the virus (e.g., AAV), and replacing with a non-native nucleic acid, such as a SGSH encoding nucleic acid sequence. Typically, for AAV one or both inverted terminal repeat (ITR) sequences of AAV genome are retained in the rAAV vector. A "recombinant" viral vector (e.g., rAAV) is distinguished from a viral (e.g., AAV) genome, since all or a part of the viral genome has been replaced with a non-native sequence with respect to the viral (e.g., AAV) genomic nucleic acid such as SGSH encoding nucleic acid sequence. Incorporation of a non-native sequence therefore defines the viral vector (e.g., AAV) as a "recombinant" vector, which in the case of AAV can be referred to as a "rAAV vector."

An AAV vector (e.g., rAAV vector) can be packaged and is referred to herein as an "AAV particle" for subsequent infection (transduction) of a cell, ex vivo, in vitro or in vivo. Where a recombinant AAV vector is encapsulated or packaged into an AAV particle, the particle can also be referred to as a "rAAV particle." In certain embodiments, an AAV particle is a rAAV particle. A rAAV particle often comprises a rAAV vector, or a portion thereof. A rAAV particle can be one or more rAAV particles (e.g., a plurality of AAV particles). rAAV particles typically comprise proteins that encapsulate or package the rAAV vector genome (e.g., capsid proteins). It is noted that reference to a rAAV vector can also be used to reference a rAAV particle.

Any suitable AAV particle (e.g., rAAV particle) can be used for a method or use herein. A rAAV particle, and/or genome comprised therein, can be derived from any suitable serotype or strain of AAV. A rAAV particle, and/or genome comprised therein, can be derived from two or more serotypes or strains of AAV. Accordingly, a rAAV can comprise proteins and/or nucleic acids, or portions thereof, of any serotype or strain of AAV, wherein the AAV particle is suitable for infection and/or transduction of a mammalian cell. Non-limiting examples of AAV serotypes include AAV1, AAV2, AAV3, AAV4, AAV5, AAV6, AAV7, AAV8, AAV9, AAV10, AAV11, AAV12, AAV-rh74, AAV-rh10 or AAV-2i8.

In certain embodiments a plurality of rAAV particles comprises particles of, or derived from, the same strain or serotype (or subgroup or variant). In certain embodiments a plurality of rAAV particles comprise a mixture of two or more different rAAV particles (e.g., of different serotypes and/or strains).

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Despite the possibility that AAV variants including capsid variants may not be serologically distinct from a reference AAV or other AAV serotype, they differ by at least one nucleotide or amino acid residue compared to the reference or other AAV serotype.

In certain embodiments, a rAAV particle excludes certain serotypes. In one embodiment, a rAAV particle is not an AAV4 particle. In certain embodiments, a rAAV particle is antigenically or immunologically distinct from AAV4. Distinctness can be determined by standard methods. For example, ELISA and Western blots can be used to determine whether a viral particle is antigenically or immunologically distinct from AAV4. Furthermore, in certain embodiments a rAAV2 particle retains tissue tropism distinct from AAV4.

In certain embodiments, a rAAV vector based upon a first serotype genome corresponds to the serotype of one or more of the capsid proteins that package the vector. For example, the serotype of one or more AAV nucleic acids (e.g., ITRs) that comprises the AAV vector genome corresponds to the serotype of a capsid that comprises the rAAV particle.

In certain embodiments, a rAAV vector genome can be based upon an AAV (e.g., AAV2) serotype genome distinct from the serotype of one or more of the AAV capsid proteins that package the vector. For example, a rAAV vector genome can comprise AAV2 derived nucleic acids (e.g., ITRs), whereas at least one or more of the three capsid proteins are derived from a different serotype, e.g., a AAV1, AAV3, AAV4, AAV5, AAV6, AAV7, AAV8, AAV9, AAV10, AAV11, AAV12, Rh10, Rh74 or AAV-2i8 serotype or variant thereof.

In certain embodiments, a rAAV particle or a vector genome thereof related to a reference serotype has a polynucleotide, polypeptide or subsequence thereof that comprises or consists of a sequence at least 60% or more (e.g., 65%, 70%, 75%, 80%, 85%, 90%, 95%, 96%, 97%, 98%, 99%, 99.1%, 99.2%, 99.3%, 99.4%, 99.5%, etc.) identical to a polynucleotide, polypeptide or subsequence of an AAV1, AAV2, AAV3, AAV4, AAV5, AAV6, AAV7, AAV8, AAV9, AAV10, AAV11, AAV12, Rh10, Rh74 or AAV-2i8 particle. In particular embodiments, a rAAV particle or a vector genome thereof related to a reference serotype has a capsid or ITR sequence that comprises or consists of a sequence at least 60% or more (e.g., 65%, 70%, 75%, 80%, 85%, 90%, 95%, 96%, 97%, 98%, 99%, 99.1%, 99.2%, 99.3%, 99.4%, 99.5%, etc.) identical to a capsid or ITR sequence of an AAV1, AAV2, AAV3, AAV4, AAV5, AAV6, AAV7, AAV8, AAV9, AAV10, AAV11, AAV12, Rh10, Rh74 or AAV-2i8 serotype.

In certain embodiments, a method herein comprises use, administration or delivery of a rAAV9 particle. In certain embodiments, a method herein comprises use, administration or delivery of a rAAV2 particle.

In certain embodiments a rAAV9 particle comprises an AAV9 capsid. In certain embodiments a rAAV9 particle comprises one or more capsid proteins (e.g., VP1, VP2 and/or VP3) that are at least 60%, 65%, 70%, 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV9 particle. In certain embodiments a rAAV9 particle comprises VP1, VP2 and VP3 capsid proteins that are at least 75% or more identical, e.g., 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV9 particle. In certain embodiments, a rAAV9 particle is a variant of a native or wild-type AAV9 particle. In some aspects, one or more capsid proteins of an AAV9 variant have 1, 2, 3, 4, 5, 5-10, 10-15, 15-20 or more amino acid substitutions compared to capsid protein(s) of a native or wild-type AAV9 particle.

In certain embodiments a rAAV2 particle comprises an AAV2 capsid. In certain embodiments a rAAV2 particle comprises one or more capsid proteins (e.g., VP1, VP2 and/or VP3) that are at least 60%, 65%, 70%, 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV2 particle. In certain embodiments a rAAV2 particle comprises VP1, VP2 and VP3 capsid proteins that are at least 75% or more identical, e.g., 80%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to a corresponding capsid protein of a native or wild-type AAV2 particle. In certain embodiments, a rAAV2 particle is a variant of a native or wild-type AAV2 particle. In some aspects, one or more capsid proteins of an AAV2 variant have 1, 2, 3, 4, 5, 5-10, 10-15, 15-20 or more amino acid substitutions compared to capsid protein(s) of a native or wild-type AAV2 particle.

In certain embodiments, a rAAV particle comprises one or two ITRs (e.g., a pair of ITRs) that are at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to corresponding ITRs of a native or wild-type AAV1, AAV2, AAV3, AAV4, AAV5, AAV6, AAV7, AAV8, AAV9, AAV10, AAV11, AAV12, AAV-rh74, AAV-rh10 or AAV-2i8, as long as they retain one or more desired ITR functions (e.g., ability to form a hairpin, which allows DNA replication; integration of the AAV DNA into a host cell genome; and/or packaging, if desired).

In certain embodiments a rAAV9 particle comprises one or two ITRs (e.g., a pair of ITRs) that are at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to corresponding ITRs of a native or wild-type AAV2 particle, as long as they retain one or more desired ITR functions (e.g., ability to form a hairpin, which allows DNA replication; integration of the AAV DNA into a host cell genome; and/or packaging, if desired).

In certain embodiments a rAAV2 particle comprises one or two ITRs (e.g., a pair of ITRs) that are at least 75% or more identical, e.g., 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 100% identical to corresponding ITRs of a native or wild-type AAV2 particle, as long as they retain one or more desired ITR functions (e.g., ability to form a hairpin, which allows DNA replication; integration of the AAV DNA into a host cell genome; and/or packaging, if desired).

A rAAV particle can comprise an ITR having any suitable number of "GAGC" repeats. In certain embodiments an ITR of an AAV2 particle comprises 1, 2, 3, 4, 5, 6, 7, 8, 9 or 10 or more "GAGC" repeats. In certain embodiments a rAAV2 particle comprises an ITR comprising three "GAGC" repeats. In certain embodiments a rAAV2 particle comprises an ITR which has less than four "GAGC" repeats. In certain embodiments a rAAV2 particle comprises an ITR which has more than four "GAGC" repeats. In certain embodiments an ITR of a rAAV2 particle comprises a Rep binding site wherein the fourth nucleotide in the first two "GAGC" repeats is a C rather than a T.

Exemplary suitable length of DNA can be incorporated in rAAV vectors for packaging/encapsidation into a rAAV particle can about 5 kilobases (kb) or less. In particular, embodiments, length of DNA is less than about 5 kb, less than about 4.5 kb, less than about 4 kb, less than about 3.5 kb, less than about 3 kb, or less than about 2.5 kb.

Recombinant AAV vectors that include a polynucleotide that directs the expression of a polypeptide can be generated using suitable recombinant techniques known in the art (e.g., see Sambrook et al., 1989). Recombinant AAV vectors are typically packaged into transduction-competent AAV particles and propagated using an AAV viral packaging system. A transduction-competent AAV particle is capable of binding to and entering a mammalian cell and subsequently delivering a nucleic acid cargo (e.g., a heterologous gene) to the nucleus of the cell. Thus, an intact rAAV particle that is transduction-competent is configured to transduce a mammalian cell. A rAAV particle configured to transduce a mammalian cell is often not replication competent, and requires additional protein machinery to self-replicate. Thus a rAAV particle that is configured to transduce a mammalian cell is engineered to bind and enter a mammalian cell and deliver a nucleic acid to the cell, wherein the nucleic acid for delivery is often positioned between a pair of AAV ITRs in the rAAV genome.

Suitable host cells for producing transduction-competent AAV particles include but are not limited to microorganisms, yeast cells, insect cells, and mammalian cells that can be, or have been, used as recipients of a heterologous rAAV vectors. Cells from the stable human cell line, HEK293 (readily available through, e.g., the American Type Culture Collection under Accession Number ATCC CRL1573) can be used. In certain embodiments a modified human embryonic kidney cell line (e.g., HEK293), which is transformed with adenovirus type-5 DNA fragments, and expresses the adenoviral E1a and E1b genes is used to generate recombinant AAV particles. The modified HEK293 cell line is readily transfected, and provides a particularly convenient platform in which to produce rAAV particles. Methods of generating high titer AAV particles capable of transducing mammalian cells are known in the art. For example, AAV particle can be made as set forth in Wright, 2008 and Wright, 2009.

In certain embodiments, AAV helper functions are introduced into the host cell by transfecting the host cell with an AAV helper construct either prior to, or concurrently with, the transfection of an AAV expression vector. AAV helper constructs are thus sometimes used to provide at least transient expression of AAV rep and/or cap genes to complement missing AAV functions necessary for productive AAV transduction. AAV helper constructs often lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. A number of other vectors are known which encode Rep and/or Cap expression products.

A "transgene" is used herein to conveniently refer to a nucleic acid/polynucleotide that is intended or has been introduced into a cell or organism. Transgenes include any nucleic acid, such as a gene that encodes a polypeptide or protein (e.g., SGSH), and are generally heterologous with respect to naturally occurring AAV genomic sequences.

The term "transduce" refers to introduction of a nucleic acid into a cell or host organism by way of a vector (e.g., an AAV particle). Introduction of a SGSH transgene into a cell by a rAAV particle is can therefore be referred to as "transduction" of the cell. The transgene may or may not be integrated into genomic nucleic acid of a transduced cell. If an introduced transgene becomes integrated into the nucleic acid (genomic DNA) of the recipient cell or organism it can be stably maintained in that cell or organism and further passed on to or inherited by progeny cells or organisms of the recipient cell or organism. Finally, the introduced transgene may exist in the recipient cell or host organism extra chromosomally, or only transiently. A "transduced cell" is therefore a cell into which the transgene has been introduced by way of transduction. Thus, a "transduced" cell is a cell into which, or a progeny thereof in which a transgene has been introduced. A transduced cell can be propagated, transgene transcribed and the encoded protein expressed. For gene therapy uses and methods, a transduced cell can be in a mammal.

Non-transduced cells refer to those into which an AAV vector has not been introduced. SGSH secretion by transduced cells can be taken up by non-transduced cells providing a benefit to those cells. Thus, SGSH secretion by transduced cells and subsequent delivery (distribution) to other regions of the CNS via cerebrospinal fluid or the vasculature can provide SGSH that is in turn taken-up by non-transduced cells.

As used herein, the term sulfamidase (SGSH) protein or polypeptide includes variants, such as SGSH having one or more amino acid substitutions, deletions and/or additions/ insertions. In particular embodiments, an SGSH variant is SEQ ID NO:1 with one or more a substitutions, deletions and/or additions/insertions. In further particular embodiments, an SGSH variant is SEQ ID NO:1 with 1-5 amino acid substitutions. In more particular embodiments, an SGSH variant is SEQ ID NO:1 with an amino acid substitution at position 264, such as an asparagine (N) to glutamine (Q) substitution.

SGSH polypeptide having SGSH activity refers to a SGSH protein or variant thereof that displays at least 50%, at least 60%, at least 70%, at least 75%, at least 80%, at least 85%, at least 90%, at least 95%, or about 100% or more of the activity or function of human wild-type SGSH of SEQ ID NO:1 using a suitable assay. In certain embodiments, a SGSH variant refers to a SGSH protein that displays at least 10%, at least 20%, at least 30%, at least 40%, at least 50%, at least 60%, at least 70%, at least 75%, at least 80%, at least 90%, or about 100% greater secretion from transduced cells than secretion of the human SGSH of SEQ ID NO:1. In certain embodiments, a SGSH variant refers to a SGSH protein that displays at least 10%, at least 20%, at least 30%, at least 40%, at least 50%, at least 60%, at least 70%, at least 75%, at least 80%, at least 90%, or about 100% greater uptake by cells than uptake of the human SGSH of SEQ ID NO:1.

A SGSH may comprise a variant form of a SGSH polypeptide that retains at least partial or all, or even greater SGSH activity. SGSH and variants thereof may be obtained from any suitable organism (e.g., from a mammal, from a human, from a non-human mammal, e.g., from a dog, pig, cow, or the like). In certain embodiments a SGSH variant has at least 60% identity, at least 70% identity, at least 75% identity, at least 80% identity, at least 85% identity, at least 90% identity, at least 95% identity, at least 96% identity, at least 97% identity, at least 98% identity, or 99% identity to the SGSH protein set forth in SEQ ID NO:1.

In certain embodiments a rAAV particle comprises an AAV capsid protein and a transgene/nucleic acid encoding SGSH. In certain embodiments a rAAV particle comprises an AAV capsid protein and a nucleic acid that directs the expression and/or secretion of a SGSH polypeptide. A representative human SGSH amino acid sequence is depicted in SEQ ID NO:1.

In certain embodiments a rAAV particle comprises an AAV capsid protein and a transgene/nucleic acid encoding a SGSH polypeptide. In certain embodiments a rAAV particle comprises an AAV capsid protein and a transgene/nucleic acid that directs the expression and/or secretion of a SGSH polypeptide. In certain embodiments, a nucleic acid being administered encodes SGSH. In certain embodiments a SGSH polypeptide has at least 60% identity, at least 70% identity, at least 75% identity, at least 80% identity, at least 85% identity, at least 90% identity, at least 95% identity, at least 96% identity, at least 97% identity, at least 98% identity, or at least 99% identity to the protein set forth in SEQ ID NO:1.

In certain embodiments a method or use includes administering or delivering rAAV-SGSH particles to a mammal and optionally administering one or more immunosuppressive agents to the mammal. In certain embodiments a method or use includes administering or delivering rAAV-SGSH particles to a mammal and optionally administering 2, 3, 4 or more immunosuppressive agents to the mammal.

In certain embodiments, an immunosuppressive agent is an anti-inflammatory agent. In certain embodiments, an immunosuppressive agent is mycophenolate, or a derivative thereof. An example of such a mycophenolate derivative is mycophenolate mofetil (MMF). In certain embodiments, an immunosuppressive agent is cyclosporine or a derivative thereof.

In certain embodiments, an immunosuppressive agent is administered before, during and/or after administration of rAAV-SGSH particles to a mammal. In certain embodiments, an immunosuppressive agent is administered concurrently with administration of rAAV-SGSH particles to a mammal. In certain embodiments, an immunosuppressive agent is administered after administration of rAAV-SGSH particles to a mammal.

A rAAV particle and/or immunosuppressive agent can be formulated in any suitable formulation suitable for a particular route of administration. Various pharmaceutically acceptable formulations are commercially available and obtainable by a medical practitioner.

A rAAV particle can be administered by any suitable route. In certain embodiments a method or use includes administering rAAV-SGSH particles to the central nervous system (CNS) of a mammal. In certain embodiments, the central nervous system includes brain, spinal cord and cerebral spinal fluid (CSF). In certain embodiments, a method or use includes administering rAAV-SGSH particles to the brain or spinal cord or CSF of a mammal. In certain embodiments, rAAV-SGSH particles are administered to a portion of brain or spinal cord.

In certain embodiments, rAAV-SGSH particles are administered to brain parenchyma, subarachnoid space and/or intrathecal space. In certain embodiments, rAAV-SGSH particles are administered to one or more of cisterna magna, intraventricular space, brain ventricle, subarachnoid space, and/or ependyma of said mammal.

In further embodiments, rAAV-SGSH particles are administered to the ventricular system. In still further embodiments, rAAV-SGSH particles are administered to one or more of the rostral lateral ventricle; and/or caudal lateral ventricle; and/or right lateral ventricle; and/or left lateral ventricle; and/or right rostral lateral ventricle; and/or left rostral lateral ventricle; and/or right caudal lateral ventricle; and/or left caudal lateral ventricle.

In certain embodiments rAAV-SGSH particles are administered to one or more cells that contact the CSF in a mammal, for example by contacting cells with rAAV-SGSH particles. Non-limiting examples of cells that contact the CSF include ependymal cells, pial cells, endothelial cells and/or meningeal cells. In certain embodiments rAAV-SGSH particles are administered to ependymal cells. In certain embodiments rAAV-SGSH particles are delivered to ependymal cells, for example by contacting ependymal cells with rAAV-SGSH particles.

In certain embodiments, rAAV-SGSH particles are administered/delivered locally. "Local delivery" refers to delivery directly to a target site within a mammal (e.g., directly to a tissue or fluid). For example, rAAV-SGSH particles can be locally delivered by direct injection into an organ, tissue or specified anatomical location. In certain embodiments, rAAV-SGSH particles are delivered or administered by direct injection to the brain, spinal cord, or a tissue or fluid thereof (e.g., CSF, such as ependymal cells, pial cells, endothelial cells and/or meningeal cells). For example rAAV-SGSH particles can be directly delivered, by way of direct injection, to the CSF, cisterna magna, intraventricular space, a brain ventricle, subarachnoid space and/or intrathecal space; and/or ependymal; and/or rostral lateral ventricle; and/or caudal lateral ventricle; and/or right lateral ventricle; and/or left lateral ventricle; and/or right rostral lateral ventricle; and/or left rostral lateral ventricle; and/or right caudal lateral ventricle; and/or left caudal lateral ventricle.

In certain embodiments, rAAV-SGSH particles are delivered to a tissue, fluid or cell of the brain or spinal cord by direct injection into a tissue or fluid of the brain or spinal cord. In certain embodiments, rAAV-SGSH particles are delivered to a tissue or fluid of the brain or spinal cord by stereotactic injection.

In certain embodiments one or more rAAV-SGSH particles are delivered or administered by direct injection to the brain, spinal cord, or portion thereof, or a tissue or fluid thereof (e.g., CSF such as ependyma). In a particular aspect, rAAV-SGSH particles transduce ependymal cells, pial cells, endothelial cells and/or meningeal cells.

In certain embodiments, a method or use includes administering rAAV particles to the brain or spinal cord, or portion thereof, of a mammal where the rAAV particles are configured to transduce brain or spinal cord cells of the mammal and direct expression of the polypeptide having SGSH activity in the brain or spinal cord of the mammal. In certain embodiments, the SGSH is expressed and/or detected in a central nervous tissue (e.g., brain, e.g., striatum, thalamus, medulla, cerebellum, occipital cortex, prefrontal cortex) distal to the administration site. In certain embodiments, the SGSH is present or detected broadly in a central nervous tissue (e.g., brain, e.g., striatum, thalamus, medulla, cerebellum, occipital cortex, and/or prefrontal cortex) that reflects distribution away from the administration site and optionally throughout a central nervous tissue (e.g., brain, e.g., striatum, thalamus, medulla, cerebellum, occipital cortex, and/or prefrontal cortex) which can be taken up by other (e.g., non-transduced) cells.

An effective amount of rAAV particles, such as rAAV-SGSH particles, can be empirically determined. Administration can be effected in one or more doses, continuously or intermittently throughout the course of treatment. Effective doses of administration can be determined by those of skill in the art and may vary according to the AAV serotype, viral titer and the weight, condition and species of mammal being treated. Single and multiple administrations (e.g., 1-5 or more) can be carried out with the dose level, target and timing being selected by the treating physician. Multiple doses may be administered as is required to maintain adequate enzyme activity, for example.

In certain embodiments, a plurality of rAAV-SGSH particles are administered. In certain embodiments, rAAV-SGSH particles are administered at a dose of about $1\times10^5$ to about $1\times10^{18}$ vg/ml in about 1 to about 5 ml; at a dose of about 1 to about 3 ml of $1\times10^7$ to about $1\times10^{16}$ vg/ml; or at a dose of about 1 to about 2 ml of $1\times10^8$ to about $1\times10^{15}$ vg/ml. In certain embodiments, rAAV-SGSH particles are administered at a dose of about $1\times10^8$ to about $1\times10^{15}$ vg/kg body weight of the mammal being treated.

In certain embodiments, rAAV-SGSH particles are administered at a dose of about $1\times10^6$ to about $1\times10^{18}$ vg/kg. For example, rAAV-SGSH particles can be administered at a dose of about 0.1-5 ml of $1\times10^7$-$1\times10^{16}$ vg/ml, about 0.5-5 ml of $1\times10^5$-$1\times10^{16}$ vg/ml, about 1-5 ml of $1\times10^5$-$1\times10^{16}$ vg/ml, about 1-3 ml of $1\times10^7$-$1\times10^{14}$ vg/ml or a dose of about 1-2 ml of $1\times10^8$-$1\times10^{13}$ vg/ml.

In certain embodiments, rAAV-SGSH particles are administered at a dose of about $1\times10^8$ vg/kg, about $5\times10^8$ vg/kg, about $1\times10^9$ vg/kg, about $5\times10^9$ vg/kg, about $1\times10^{10}$ vg/kg, about $5\times10^{10}$ vg/kg, about $1\times10^{11}$ vg/kg, about $5\times10^{11}$ vg/kg, about $1\times10^{12}$ vg/kg, about $5\times10^{12}$ vg/kg, about $1\times10^{13}$ vg/kg, about $5\times10^{13}$ vg/kg, about $1\times10^{14}$ vg/kg, about $5\times10^{14}$ vg/kg, or about $1\times10^{15}$ vg/kg body weight of the mammal being treated.

As used herein the term "pharmaceutically acceptable" and "physiologically acceptable" mean a biologically acceptable composition, formulation, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Such composition, "pharmaceutically acceptable" and "physiologically acceptable" formulations and compositions can be sterile. Such pharmaceutical formulations and compositions may be used, for example in administering a rAAV-SGSH particle to a subject.

Such formulations and compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Supplementary active compounds (e.g., preservatives, antibacterial, antiviral and antifungal agents) can also be incorporated into the formulations and compositions.

Pharmaceutical compositions typically contain a pharmaceutically acceptable excipient. Such excipients include any pharmaceutical agent that does not itself induce the production of antibodies harmful to the individual receiving the composition, and which may be administered without undue toxicity. Pharmaceutically acceptable excipients include, but are not limited to, sorbitol, Tween80, and liquids such as water, saline, glycerol and ethanol. Pharmaceutically acceptable salts can be included therein, for example, mineral acid salts such as hydrochlorides, hydrobromides, phosphates, sulfates, and the like; and the salts of organic acids such as acetates, propionates, malonates, benzoates, and the like. Additionally, auxiliary substances, such as surfactants, wetting or emulsifying agents, pH buffering substances, and the like, may be present in such vehicles.

Pharmaceutical compositions can be formulated to be compatible with a particular route of administration or delivery, as set forth herein or known to one of skill in the art. Thus, pharmaceutical compositions include carriers, diluents, or excipients suitable for administration or delivery by various routes.

Pharmaceutical forms suitable for injection or infusion of rAAV particles, such as rAAV-SGSH particles, can include sterile aqueous solutions or dispersions which are adapted for the extemporaneous preparation of sterile injectable or infusible solutions or dispersions, optionally encapsulated in liposomes. In all cases, the ultimate form should be a sterile fluid and stable under the conditions of manufacture, use and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Isotonic agents, for example, sugars, buffers or salts (e.g., sodium chloride) can be included. Prolonged absorption of injectable compositions can be brought about by the use in the compositions of agents delaying absorption, for example, aluminum monostearate and gelatin.

Solutions or suspensions of rAAV-SGSH particles can optionally include one or more of the following components: a sterile diluent such as water for injection, saline solution, such as phosphate buffered saline (PBS), artificial CSF, a surfactants, fixed oils, a polyol (for example, glycerol, propylene glycol, and liquid polyethylene glycol, and the like), glycerin, or other synthetic solvents; antibacterial and antifungal agents such as parabens, chlorobutanol, phenol, ascorbic acid, and the like; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose.

Pharmaceutical formulations, compositions and delivery systems appropriate for the compositions, methods and uses of the invention are known in the art (see, e.g., *Remington: The Science and Practice of Pharmacy* (2003) 20$^{th}$ ed., Mack Publishing Co., Easton, PA; *Remington's Pharmaceutical Sciences* (1990) 18$^{th}$ ed., Mack Publishing Co., Easton, PA; *The Merck Index* (1996) 12$^{th}$ ed., Merck Publishing Group, Whitehouse, NJ; *Pharmaceutical Principles of Solid Dosage Forms* (1993), Technonic Publishing Co., Inc., Lancaster, Pa.; Ansel and Stoklosa, *Pharmaceutical Calculations* (2001) 11$^{th}$ ed., Lippincott Williams & Wilkins, Baltimore, MD; and Poznansky et al., *Drug Delivery Systems* (1980), R. L. Juliano, ed., Oxford, N.Y., pp. 253-315).

rAAV particles, such as rAAV-SGSH particles, and their compositions may be formulated in dosage unit form for ease of administration and uniformity of dosage. Dosage unit form as used herein refers to physically discrete units suited as unitary dosages for an individual to be treated; each unit containing a predetermined quantity of active compound calculated to produce the desired therapeutic effect in association with the required pharmaceutical carrier. The dosage unit forms are dependent upon the amount of rAAV particles (e.g., rAAV-SGSH particles) believed necessary to produce the desired effect(s). The amount necessary can be formulated in a single dose, or can be formulated in multiple dosage units. The dose may be adjusted to a suitable rAAV particles concentration, optionally combined with an anti-inflammatory agent, and packaged for use.

In one embodiment, pharmaceutical compositions will include sufficient genetic material (rAAV particles) to provide a therapeutically effective amount, i.e., an amount sufficient to reduce or ameliorate symptoms or an adverse effect of a disease state in question or an amount sufficient to confer the desired benefit.

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. Thus, for example, rAAV-SGSH particles, and pharmaceutical compositions thereof can be packaged in single or multiple unit dosage form for ease of administration and uniformity of dosage.

Formulations containing rAAV-SGSH particles typically contain an effective amount, the effective amount being readily determined by one skilled in the art. The rAAV-SGSH particles may typically range from about 1% to about 95% (w/w) of the composition, or even higher if suitable. The quantity to be administered depends upon factors such as the age, weight and physical condition of the mammal or the human subject considered for treatment. Effective dosages can be established by one of ordinary skill in the art through routine trials establishing dose response curves.

In certain embodiments a method includes administering a plurality of rAAV-SGSH particles to a mammal as set forth herein, where severity, frequency, progression or time of onset of one or more symptoms of a deficiency or defect in SGSH expression or function (e.g., MPSIIIA) are decreased, reduced, prevented, inhibited or delayed. In certain embodiments a method includes administering a plurality of rAAV-SGSH particles to a mammal to treat a symptom or adverse effect of MPIIIA. In certain embodiments a method includes administering a plurality of rAAV-SGSH particles to a mammal to stabilize, delay or prevent worsening, or progression, or reverse a symptom or adverse effect of MPSIIIA.

In certain embodiments a method includes administering a plurality of AAV-SGSH particles to the central nervous system, or portion thereof as set forth herein, of a mammal and severity, frequency, progression or time of onset of one or more symptoms of a deficiency or defect in SGSH expression or function (e.g., MPSIIIA) are decreased, reduced, prevented, inhibited or delayed by at least about 5 to about 10, about 10 to about 25, about 25 to about 50, or about 50 to about 100 days.

In certain embodiments, a symptom or adverse effect comprises an early stage or late stage symptom; a behavior, personality or language symptom; sleep disturbance; and/or a cognitive symptom.

Examples of early symptoms/adverse effects of MPSIIIA treatable according to the methods and uses herein include improvements or slowing or preventing progression or worsening of delayed speech and behavior problems. Other symptoms of MPSIIIA include reducing or correcting restlessness, aggressive or destructive behavior or anxiety. In some instances, symptoms include autism spectrum disorder, a condition characterized by difficulty with social interactions and communication. Other symptoms of MPSIIIA include sleep disturbances. As MPSIIIA advances, further symptoms include inhibition, loss of or worsening of intellectual capability and/or development as well as developmental regression or the loss of previously acquired skills. In later stages of MPSIIIA, people may develop seizures and movement disorders. Invention methods and uses include those directed to treatment or improvement, or reducing severity or frequency of any or all of the foregoing symptoms of MPSIIIA.

The terms "polynucleotide," "nucleic acid" and "transgene" are used interchangeably herein to refer to all forms of nucleic acid, oligonucleotides, including deoxyribonucleic acid (DNA) and ribonucleic acid (RNA) and polymers thereof. Polynucleotides include genomic DNA, cDNA and antisense DNA, and spliced or unspliced mRNA, rRNA, tRNA and inhibitory DNA or RNA (RNAi, e.g., small or short hairpin (sh)RNA, microRNA (miRNA), small or short interfering (si)RNA, trans-splicing RNA, or antisense RNA). Polynucleotides can include naturally occurring, synthetic, and intentionally modified or altered polynucleotides (e.g., variant nucleic acid). Polynucleotides can be single stranded, double stranded, or triplex, linear or circular, and can be of any suitable length. In discussing polynucleotides, a sequence or structure of a particular polynucleotide may be described herein according to the convention of providing the sequence in the 5' to 3' direction.

A nucleic acid encoding a polypeptide often comprises an open reading frame that encodes the polypeptide. Unless otherwise indicated, a particular nucleic acid sequence also includes degenerate codon substitutions.

Nucleic acids can include one or more expression control or regulatory elements operably linked to the open reading frame, where the one or more regulatory elements are configured to direct the transcription and translation of the polypeptide encoded by the open reading frame in a mammalian cell. Non-limiting examples of expression control/regulatory elements include transcription initiation sequences (e.g., promoters, enhancers, a TATA box, and the like), translation initiation sequences, mRNA stability sequences, poly A sequences, secretory sequences, and the like. Expression control/regulatory elements can be obtained from the genome of any suitable organism.

A "promoter" refers to a nucleotide sequence, usually upstream (5') of a coding sequence, which directs and/or controls the expression of the coding sequence by providing the recognition for RNA polymerase and other factors required for proper transcription. "Promoter" includes a minimal promoter that is a short DNA sequence comprised of a TATA-box and optionally other sequences that serve to specify the site of transcription initiation, to which regulatory elements are added for control of expression.

An "enhancer" is a DNA sequence that can stimulate transcription activity and may be an innate element of the promoter or a heterologous element that enhances the level or tissue specificity of expression. It is capable of operating in either orientation (5'→3' or 3'→5'), and may be capable of functioning even when positioned either upstream or downstream of the promoter.

Promoters and/or enhancers may be derived in their entirety from a native gene, or be composed of different elements derived from different elements found in nature, or even be comprised of synthetic DNA segments. A promoter or enhancer may comprise DNA sequences that are involved in the binding of protein factors that modulate/control effectiveness of transcription initiation in response to stimuli, physiological or developmental conditions.

Non-limiting examples include SV40 early promoter, mouse mammary tumor virus LTR promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, pol II promoters, pol III promoters, synthetic promoters, hybrid promoters, and the like. In addition, sequences derived from non-viral genes, such as the murine metallothionein gene, will also find use herein. Exemplary constitutive promoters include the promoters for the following genes which encode certain constitutive or "housekeeping" functions: hypoxanthine phosphoribosyl transferase (HPRT), dihydrofolate reductase (DHFR), adenosine deaminase, phosphoglycerol kinase (PGK), pyruvate kinase, phosphoglycerol mutase, the actin promoter, and other constitutive promoters known to those of skill in the art. In addition, many viral promoters function constitutively in eukaryotic cells. These include: the early and late promoters of SV40; the long terminal repeats (LTRs) of Moloney Leukemia Virus and other retroviruses; and the thymidine kinase promoter of Herpes Simplex Virus, among many others. Accordingly, any of the above-referenced constitutive promoters can be used to control transcription of a heterologous gene insert.

Transgenes under control of inducible promoters are expressed only or to a greater degree, in the presence of an inducing agent, (e.g., transcription under control of the metallothionein promoter is greatly increased in presence of certain metal ions). Inducible promoters include responsive elements (REs) which stimulate transcription when their inducing factors are bound. For example, there are REs for serum factors, steroid hormones, retinoic acid and cyclic AMP. Promoters containing a particular RE can be chosen in order to obtain an inducible response and in some cases, the RE itself may be attached to a different promoter, thereby conferring inducibility to the recombinant gene. Thus, by selecting a suitable promoter (constitutive versus inducible; strong versus weak), it is possible to control both the existence and level of expression of a polypeptide in the genetically modified cell. If the gene encoding the polypeptide is under the control of an inducible promoter, delivery of the polypeptide in situ is triggered by exposing the genetically modified cell in situ to conditions for permitting transcription of the polypeptide, e.g., by intraperitoneal injection of specific inducers of the inducible promoters which control transcription of the agent. For example, in situ expression by genetically modified cells of a polypeptide encoded by a gene under the control of the metallothionein promoter, is enhanced by contacting the genetically modified cells with a solution containing the appropriate (i.e., inducing) metal ions in situ.

A nucleic acid/transgene is "operably linked" when it is placed into a functional relationship with another nucleic acid sequence. A nucleic acid/transgene encoding a polypeptide, or a nucleic acid directing expression of a SGSH polypeptide (e.g., a polypeptide having SGSH activity) may include an inducible promoter, or a tissue-specific promoter for controlling transcription of the encoded polypeptide.

In certain embodiments, CNS-specific or inducible promoters, enhancers and the like, are employed in the methods and uses described herein. Non-limiting examples of CNS-specific promoters include those isolated from the genes from myelin basic protein (MBP), glial fibrillary acid protein (GFAP), and neuron specific enolase (NSE). Non-limiting examples of inducible promoters include DNA responsive elements for ecdysone, tetracycline, hypoxia and IFN.

In certain embodiments, an expression control element comprises a CMV enhancer. In certain embodiments, an expression control element comprises a beta actin promoter. In certain embodiments, an expression control element comprises a chicken beta actin promoter. In certain embodiments, an expression control element comprises a CMV enhancer and a chicken beta actin promoter.

As used herein, the terms "modify" or "variant" and grammatical variations thereof, mean that a nucleic acid, polypeptide or subsequence thereof deviates from a reference sequence. Modified and variant sequences may therefore have substantially the same, greater or less expression, activity or function than a reference sequence, but at least retain partial activity or function of the reference sequence. A particular type of variant is a mutant protein, which refers to a protein encoded by a gene having a mutation, e.g., a missense or nonsense mutation in SGSH.

A "nucleic acid" or "polynucleotide" variant refers to a modified sequence which has been genetically altered compared to wild-type. The sequence may be genetically modified without altering the encoded protein sequence. Alternatively, the sequence may be genetically modified to encode a variant protein, e.g., a variant SGSH protein. A nucleic acid or polynucleotide variant can also refer to a combination sequence which has been codon modified to encode a protein that still retains at least partial sequence identity to a reference sequence, such as wild-type protein sequence, and also has been codon-modified to encode a variant protein. For example, some codons of such a nucleic acid variant will be changed without altering the amino acids of a SGSH protein encoded thereby, and some codons of the nucleic acid variant will be changed which in turn changes the amino acids of a SGSH protein encoded thereby.

The terms "protein" and "polypeptide" are used interchangeably herein. The "polypeptides" encoded by a "nucleic acid" or "polynucleotide" or "transgene" disclosed herein include partial or full-length native SGSH sequences, as with naturally occurring wild-type and functional polymorphic proteins, functional subsequences (fragments) thereof, and sequence variants thereof, so long as the polypeptide retains some degree of SGSH activity. Accordingly, in methods and uses of the invention, such polypeptides encoded by nucleic acid sequences are not required to be identical to the endogenous SGSH protein that is defective, or whose activity, function, or expression is insufficient, deficient or absent in a treated mammal.

Non-limiting examples of modifications include one or more nucleotide or amino acid substitutions (e.g., about 1 to about 3, about 3 to about 5, about 5 to about 10, about 10 to about 15, about 15 to about 20, about 20 to about 25, about 25 to about 30, about 30 to about 40, about 40 to about 50, about 50 to about 100, about 100 to about 150, about 150 to about 200, about 200 to about 250, about 250 to about 500, about 500 to about 750, about 750 to about 1000 or more nucleotides or residues).

An example of an amino acid modification is a conservative amino acid substitution or a deletion. In particular embodiments, a modified or variant sequence (e.g., SGSH) retains at least part of a function or activity of the unmodified sequence (e.g., wild-type SGSH). In further particular embodiments, a modified or variant sequence (e.g., SGSH) exhibits improved secretion by cells compared to the unmodified sequence (e.g., wild-type SGSH). In still further particular embodiments, a modified or variant sequence (e.g., SGSH) exhibits improved uptake by cells compared to uptake of the unmodified sequence (e.g., wild-type SGSH).

Another example of an amino acid modification is a targeting peptide introduced into a capsid protein of an AAV particle. Peptides have been identified that target rAAV vectors, to the central nervous system, such as vascular endothelial cells. Thus, for example, endothelial cells lining brain blood vessels can be targeted by the modified rAAV particles. rAAV-SGSH particle bearing capsid proteins modified to include such peptides can be used to introduce SGSH into the central nervous system (e.g., the brain, spinal cord, etc.) as set forth herein.

A rAAV so modified may preferentially bind to one type of tissue (e.g., CNS tissue) over another type of tissue (e.g., liver tissue). In certain embodiments, a rAAV bearing a modified capsid protein may "target" brain vascular epithelia tissue by binding at level higher than a comparable, unmodified capsid protein. For example, a rAAV having a modified capsid protein may bind to brain vascular epithelia tissue at a level 50% to 100% greater than an unmodified rAAV.

A "nucleic acid fragment" is a portion of a given nucleic acid molecule. Deoxyribonucleic acid (DNA) in the majority of organisms is the genetic material while ribonucleic acid (RNA) is involved in the transfer of information contained within DNA into proteins. Fragments and variants of the disclosed nucleotide sequences and proteins or partial-length proteins encoded thereby are also encompassed by the present invention. By "fragment" or "portion" is meant a full length or less than full length of the nucleotide sequence encoding, or the amino acid sequence of, a polypeptide or protein. In certain embodiments, the fragment or portion is biologically functional (i.e., retains 5%, 10%, 15%, 20%, 25%, 30%, 35%, 40%, 45%, 50%, 55%, 60%, 65%, 70%, 75%, 80%, 85%, 90%, 95%, 99% or 100% of activity or function of wild-type SGSH).

A "variant" of a molecule is a sequence that is substantially similar to the sequence of the native molecule. For nucleotide sequences, variants include those sequences that, because of the degeneracy of the genetic code, encode the identical amino acid sequence of the native protein. Naturally occurring allelic variants such as these can be identified with the use of molecular biology techniques, as, for example, with polymerase chain reaction (PCR) and hybridization techniques. Variant nucleotide sequences also include synthetically derived nucleotide sequences, such as those generated, for example, by using site-directed mutagenesis, which encode the native protein, as well as those that encode a polypeptide having amino acid substitutions. Generally, nucleotide sequence variants of the invention will have at least 40%, 50%, 60%, to 70%, e.g., 71%, 72%, 73%, 74%, 75%, 76%, 77%, 78%, to 79%, generally at least 80%, e.g., 81%-84%, at least 85%, e.g., 86%, 87%, 88%, 89%, 90%, 91%, 92%, 93%, 94%, 95%, 96%, 97%, to 98%, sequence identity to the native (endogenous) nucleotide sequence. In certain embodiments, the variant is biologically functional (i.e., retains 5%, 10%, 15%, 20%, 25%, 30%, 35%, 40%, 45%, 50%, 55%, 60%, 65%, 70%, 75%, 80%, 85%, 90%, 95%, 99% or 100% of activity or function of wild-type SGSH).

"Conservative variations" of a particular nucleic acid sequence refers to those nucleic acid sequences that encode identical or essentially identical amino acid sequences. Because of the degeneracy of the genetic code, a large number of functionally identical nucleic acids encode any given polypeptide. For instance, the codons CGT, CGC, CGA, CGG, AGA and AGG all encode the amino acid arginine. Thus, at every position where an arginine is specified by a codon, the codon can be altered to any of the corresponding codons described without altering the encoded protein. Such nucleic acid variations are "silent variations," which are one species of "conservatively modified variations." Every nucleic acid sequence described herein that encodes a polypeptide also describes every possible silent variation, except where otherwise noted. One of skill in the art will recognize that each codon in a nucleic acid (except ATG, which is ordinarily the only codon for methionine) can be modified to yield a functionally identical molecule by standard techniques. Accordingly, each "silent variation" of a nucleic acid that encodes a polypeptide is implicit in each described sequence.

The term "substantial identity" of polynucleotide sequences means that a polynucleotide comprises a sequence that has at least 70%, 71%, 72%, 73%, 74%, 75%, 76%, 77%, 78%, or 79%, or at least 80%, 81%, 82%, 83%, 84%, 85%, 86%, 87%, 88%, or 89%, or at least 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, at least 80%, 90%, or even at least 95%.

The term "substantial identity" in the context of a polypeptide indicates that a polypeptide comprises a sequence with at least 70%, 71%, 72%, 73%, 74%, 75%, 76%, 77%, 78%, or 79%, or 80%, 81%, 82%, 83%, 84%, 85%, 86%, 87%, 88%, or 89%, or at least 90%, 91%, 92%, 93%, or 94%, or even, 95%, 96%, 97%, 98% or 99%, sequence identity to the reference sequence over a specified comparison window. An indication that two polypeptide sequences are substantially identical is that one polypeptide is immunologically reactive with antibodies raised against the second polypeptide. Thus, a polypeptide is substantially identical to a second polypeptide, for example, where the two peptides differ only by a conservative substitution.

The invention provides kits with packaging material and one or more components therein. A kit typically includes a label or packaging insert including a description of the components or instructions for use in vitro, in vivo, or ex vivo, of the components therein. A kit can contain a collection of such components, e.g., a nucleic acid, recombinant vector, rAAV-SGSH particles and optionally a second active, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include information on a disease for which a kit component may be used. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, or an electrical storage media such as RAM and ROM or hybrids of these such as magnetic/optical storage media, FLASH memory, hybrids and memory type cards.

The term "about" at used herein refers to a values that is within 10% (plus or minus) of a reference value.

The terms "treat" and "treatment" refer to both therapeutic treatment and prophylactic or preventative measures, wherein the object is to prevent, inhibit, reduce, or decrease an undesired physiological change or disorder, such as the development, progression or worsening of the disorder. For purposes of this invention, beneficial or desired clinical results include, but are not limited to, alleviation of symptoms, diminishment of extent of disease, stabilizing a (i.e., not worsening or progressing) symptom or adverse effect of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those predisposed (e.g., as determined by a genetic assay), such as those identified to be homozygous ($Sgsh^{-/-}$) with respect to lost or reduced SGSH expression or function or heterozygous ($Sgsh^{+/-}$) with respect to lost or reduced SGSH expression or function.

The terms "comprising," "having," "including," and "containing" are to be construed as open-ended terms (i.e., meaning "including, but not limited to") unless otherwise noted.

All methods and uses described herein can be performed in any suitable order unless otherwise indicated herein or otherwise clearly contradicted by context. The use of any and all examples, or exemplary language (e.g., "such as" or "for example") provided herein, is intended merely to better illuminate the invention and does not pose a limitation on the scope of the invention unless otherwise claimed. No language in the specification should be construed as indicating any non-claimed element as essential to the practice of the invention.

All of the features disclosed herein may be combined in any combination. Each feature disclosed in the specification may be replaced by an alternative feature serving a same, equivalent, or similar purpose. Thus, unless expressly stated otherwise, disclosed features (e.g., modified nucleic acid, vector, plasmid, a recombinant vector (e.g., rAAV) sequence, vector genome, or rAAV particle) are an example of a genus of equivalent or similar features.

As used herein, the forms "a", "and," and "the" include singular and plural referents unless the context clearly indicates otherwise. Thus, for example, reference to "a nucleic acid" includes a plurality of such nucleic acids, reference to "a vector" includes a plurality of such vectors, and reference to "a virus" or "AAV or rAAV particle" includes a plurality of such virions/AAV or rAAV particles.

Recitation of ranges of values herein are merely intended to serve as a shorthand method of referring individually to each separate value falling within the range, unless otherwise indicated herein, and each separate value is incorporated into the specification as if it were individually recited herein.

Accordingly, all numerical values or numerical ranges include integers within such ranges and fractions of the values or the integers within ranges unless the context clearly indicates otherwise. Thus, to illustrate, reference to 80% or more identity, includes 81%, 82%, 83%, 84%, 85%, 86%, 87%, 88%, 89%, 90%, 91%, 92%, 93%, 94% etc., as well as 81.1%, 81.2%, 81.3%, 81.4%, 81.5%, etc., 82.1%, 82.2%, 82.3%, 82.4%, 82.5%, etc., and so forth.

Reference to an integer with more (greater) or less than includes any number greater or less than the reference number, respectively. Thus, for example, a reference to less than 100, includes 99, 98, 97, etc. all the way down to the number one (1); and less than 10, includes 9, 8, 7, etc. all the way down to the number one (1).

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, 1,000-1,500, 1,500-2,000, 2,000-2,500, 2,500-3,000, 3,000-3,500, 3,500-4,000, 4,000-4,500, 4,500-5,000, 5,500-6,000, 6,000-7,000, 7,000-8,000, or 8,000-9,000, includes ranges of 10-20, 10-50, 30-50, 50-100, 100-300, 100-1,000, 1,000-3,000, 2,000-4,000, 4,000-6,000, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed.

EXAMPLES

Example 1

Material and Methods

Construction of Lysosomal Enzymes and Relative Variants Expression Vectors

Human SGSH, TPP1 and β-glu genes were PCR amplified from the human cDNA library and cloned into AAV backbone plasmid. SGSH variants were constructed by overlap PCR.

Lysosomal Enzymes Activity Assay

Lysosomal enzymes activity assay was measured by fluorogenic substrates. SGSH activity was measured by a two-step protocol (see, e.g., Karpova et al. *Journal of Inherited Metabolic Disease* 19:278-285 (1996)). Briefly, the first step involved the incubation of 10 μl of sample with 20 μl of 4-methylumbelliferyl (MU)-αGlcNs substrate (5 mM in 29 mM barbital/acetate buffer, pH 6.5) for 17 hours at 37° C. The second step continued with incubation of the sample with 10 μl of α-glucosidase (10 U/ml in 0.2% BSA) for 24 hours at 37° C. The reaction was terminated by adding 200 μl of stop buffer (500 mM carbonate buffer with 0.025% Triton X-100, pH 10.7). 4-MU was used as the standard. Fluorescence was measured at 390 nm excitation and 460 nm emission.

TPP1 activity was assayed by a modification of the methods described previously (see, e.g., Tian, et al. *Journal of Biological Chemistry* 281:6559-6572 (2006); Katz, M. L. et al. *Science Translational Medicine* 7:313ra180 (2015)) Briefly, 10 μl of sample was incubated with 90 μl of Ala-Ala-Phe 7-amido-4-methylcoumarin substrate (250 μM in 100 mM sodium citrate buffer, with 150 mM NaCl, and 0.1% Triton X-100 pH 4.0, Sigma) at 37° C. Purified recombinant TPP1 was used as the standard (gift from P. Lobel, State University of New Jersey). Plates were read with a 460-nm emission filter.

β-glu activity was assayed with 4-MU-β-D-glucuronide (10 mM in 100 mM acetate buffer, pH4.8, Sigma) as substrate (see, e.g., Liu, et al. The *Journal of Neuroscience: The Official Journal of the Society for Neuroscience* 25:9321-9327 (2005)). Stop buffer (500 mM carbonate buffer with 0.025% Triton X-100, pH 10.7) was added to terminate the reaction after 1 h of incubation at 37° C. 4-MU was used as the standard. Fluorescence was measured at 390 nm excitation and 460 nm emission.

In Vitro Lysosomal Enzymes Secretion Study

Lower passage of HEK 293 cells were maintained in DMEM medium with 10% FBS. 24 hours before transfection, $4 \times 10^4$ cells were seeded into 96 wells plate in 100 μl medium. The cells were transfected with 100 ng of plasmid using Lipofectamine™ 2000 (Invitrogen). After a setting time of transfection (24 h, 48 h or 72 h based on different experiments), 100 μl of the conditioned medium was harvested. Cells were collected by addition of 100 μl of lysate buffer (0.1% Triton X-100 in normal saline with complete protease inhibitor cocktail, Roche). Soluble lysosomal enzymes were release from cells by sonication for 2 sec twice on ice. Insoluble material was removed by centrifugation at $21 \times 10^3$ g for 15 min at 4° C. 10 μl of sample from conditioned medium or cell lysate was used for enzyme activity assay. The same samples were also used for western blot analysis.

Western Blot

20 μl of sample from cell lysate or medium was loaded into 4-12% SDS-PAGE gel and transferred to 0.45 μm PVDF membrane. Primary antibody mouse anti SGSH 1:2000 (gifted from Shire); secondary antibody HRP labeled goat anti mouse, 1:20,000 (Cell Signaling). Blots were developed using ECL Plus Western Blotting Detection System (GE Healthcare) and exposed to film for images. Protein quantification was performed using the ChemiDoc™ Imaging System (Biorad).

SGSH Enzyme Uptake Study

Human MPS IIIA fibroblast cells were maintained in DMEM medium with 10% FBS. $1.0 \times 10^5$ of cells were seeded into 24 wells plate. After 24 h later, when the cells reached 90% confluency, the medium was changed into 300 μl of conditioned medium containing SGSH activity of 100 nmol/17 h/ml derived from transfected HEK 293 cells with wtSGSH or SGSHv4 plasmid and in the absence or presence of M6P (10 mM final concentration). After 6 hours of incubation, the conditioned medium was removed and the cells were washed with 500 µl of HBSS with $Ca^{2+}$ and $Mg^{2+}$ three times. The cells were harvested and processed for the activity assay or western blot. The same cells were also processed for immunohistology Immunofluorescence Microscopy Cells were washed with 500 µl of HBSS with $Ca^{2+}$ and $Mg^{2+}$ three times and fixed with 4% paraformaldehyde in PBS for 10 min at room temperature and blocked and permeabilized (10% goat serum and 0.1% Triton X-100 in PBS) for 1 h at room temperature. Cells were incubated with mouse anti SGSH primary antibody (1:200) in PBS containing 2% goat serum overnight at 4° C., then Alexa-conjugated secondary antibody (Invitrogen) at 1:2000 for 1 h at room temperature. Cells were coverslipped with Fluoro-Gel mounting media (Electron Microscopy Sciences) and analyzed by fluorescent microscopy (Leica Microsystems)

Animals, AAV Vector Administration and Tissue Collection

MPS IIIA mice in B6.Cg-Sgsh$^{mps3a}$/PstJ strain, carrying a spontaneous mutation at the Sgsh locus, were purchased from The Jackson Laboratory (see, e.g., Bhattacharyya, et al. *Glycobiology* 11:99-103 (2001); Bhaumik et al. *Glycobiology* 9:1389-1396 (1999)), maintained at an animal facility and following an approved IACUC protocol. AAV4 vectors encoding wtSGSH or SGSHv4 enzyme were produced by triple transfection in HEK 293 cells and CsCl purification. Eight week old MPS IIIA mice disease (Sgsh$^{-/-}$) or heterozygous (Sgsh$^{-/-}$) mice were anesthetized with isoflurane. The AAV vector ($5 \times 10^{10}$ gp) was stereotaxically injected into the lateral ventricles (A/P −2.18-mm, M/L −2.9 mm, D/V −3.5 mm). The mice were sacrificed after behavioral testing was complete. CSF was collected by glass capillary through cisterna magna under dissecting microscope. After CSF collection, the mouse was perfused with cold PBS and brain regions were harvested. The brain tissues were homogenized in 200 µl ice-cold homogenization buffer (0.1% Triton X-100 in normal saline with complete protease inhibitor cocktail, Roche) for enzyme activities assay.

Morris Water Maze

Morris water maze was performed as previously described (see, e.g., Vorhees, C. V. & Williams, M. T. *Nature Protocols* 1:848-858 (2006)). Briefly, a 100 cm in diameter pool was filled with ¾ full of water, clouded with titanium (IV) oxide (Sigma). The pool was arbitrarily divided into quadrants. A transparent platform was placed 0.5 cm below the surface of the water in one quadrant (named target quadrant). Mice went through a 5 days of acquisition phase. They were given four trials each day during the acquisition phase. In each trial, the mice were released into the water facing the wall. They had 60 sec to locate the platform and stayed on the platform for 15 sec. If this was not achieved, they were guided to platform. In each trial, the latency to find the platform was recorded. Probe trial was performed at the 6th day. The platform was removed and the start position was in the quadrant opposite to the target one. The trial length was 60 sec. Time spent and distance traveled in the target quadrant were recorded. The data were analyzed by Any-maze behavioral tracking software (ANY-maze).

Example 2

Native SGSH is relatively poorly secreted.

Figure 2:
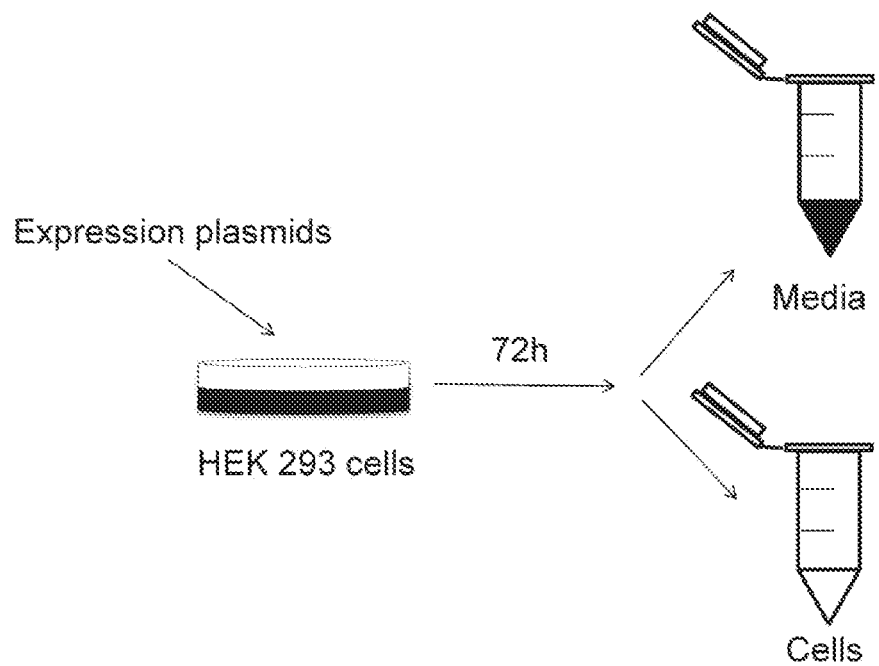
FIG. 2 shows evaluating secretion of lysosomal enzymes in vitro.
Figure 3:
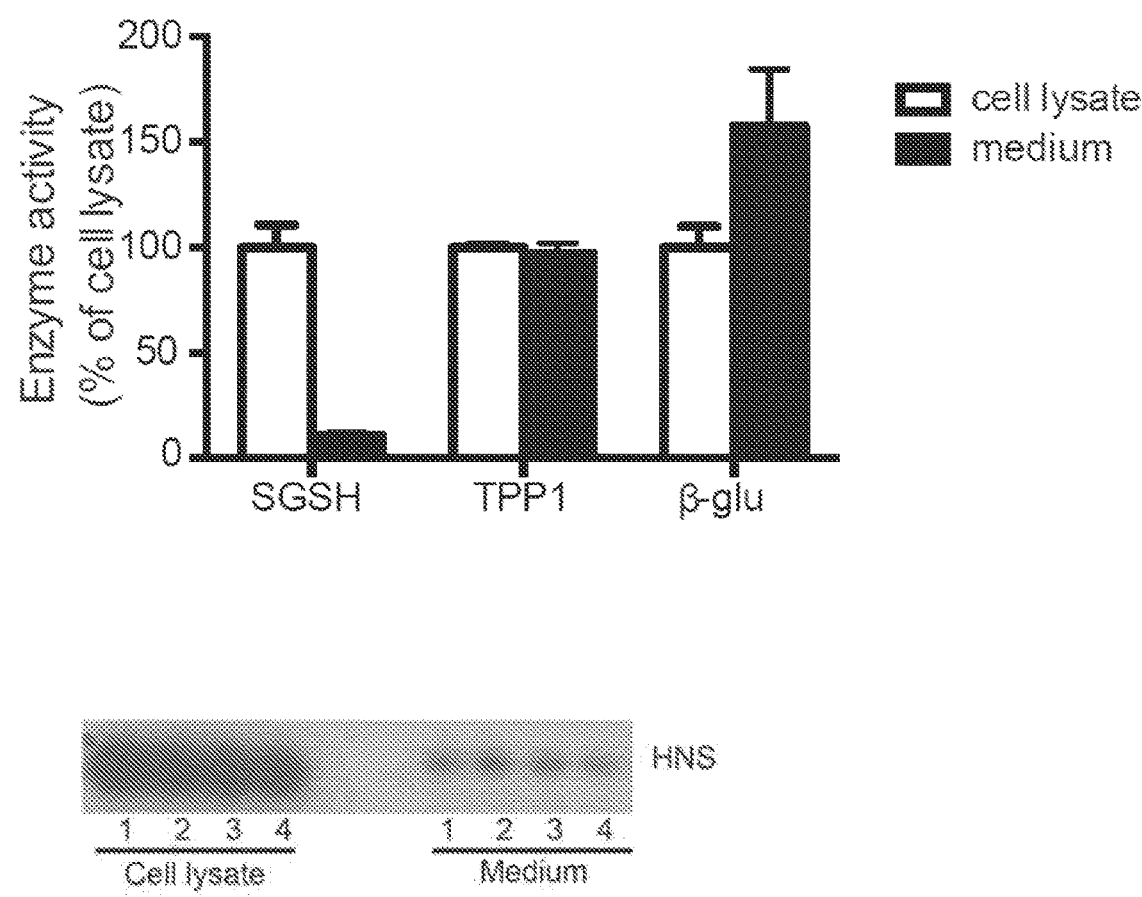
FIG. 3 shows that native SGSH is poorly secreted.

To compare the secretory potential of SGSH with tripeptidyl peptidase 1 (TPP1) and (β-glucuronidase (β-glu), HEK 293 cells were transfected with identical expression plasmids except for the recombinant protein coding sequence (FIG. 2). After 72 hours, the lysosomal enzyme activity in collected media and cell lysates were analyzed. As shown in FIG. 3, less than 20% of SGSH activity was detected in media compared to the cell lysate, while in TPP1- or β-glu-expressing cells, roughly 50% and 75-80% was secreted, respectively. This finding was mirrored when evaluating the total levels of protein by western blot (FIG. 3).

Variant SGSH Shows Improved Secretion and Uptake

Posttranslational modification of mannose or M6P on lysosomal enzymes occurs at N-linked oligosaccharide side chains. SGSH has five potential N-glycosylation consensus sequences (Asn-Xaa-Ser/Thr), with the glycan accepting Asn residue at amino acid positions 41, 142, 151, 264 and 413. Five SGSH enzyme variants were constructed with sequentially substituted Asn-to-Gln as indicated (FIG. 4A), and their secretory and uptake properties evaluated.

Most SGSH variants were indistinguishable from the wildtype protein, one variant lost enzyme activity (SGSHv3) (FIG. 4B), and one variant, SGSHv4, showed approximately twice the levels of SGSH activity in media. Additionally, SGSHv4 expressing cells showed lower levels of SGSH activity in cells; ~60% that of wild type transfected cells. These data indicate that SGSHv4 improves secretion and at the same time reduces the overload of additional SGSH within transfected cells (FIG. 4B).

Figure 5A:
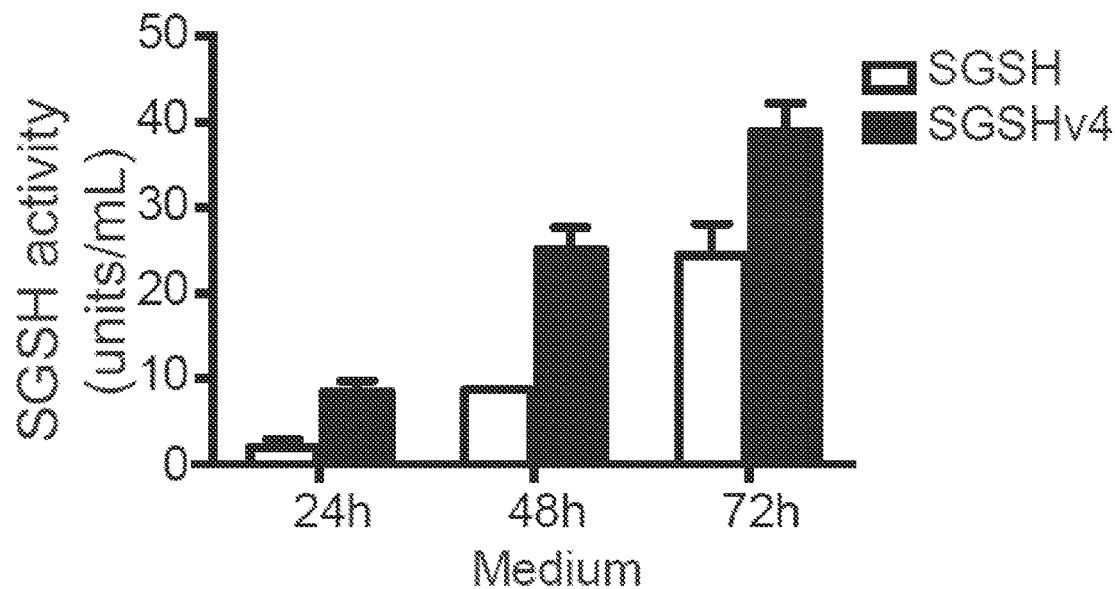
FIG. 5A shows SGSHv4 properties (media).
Figure 5B:
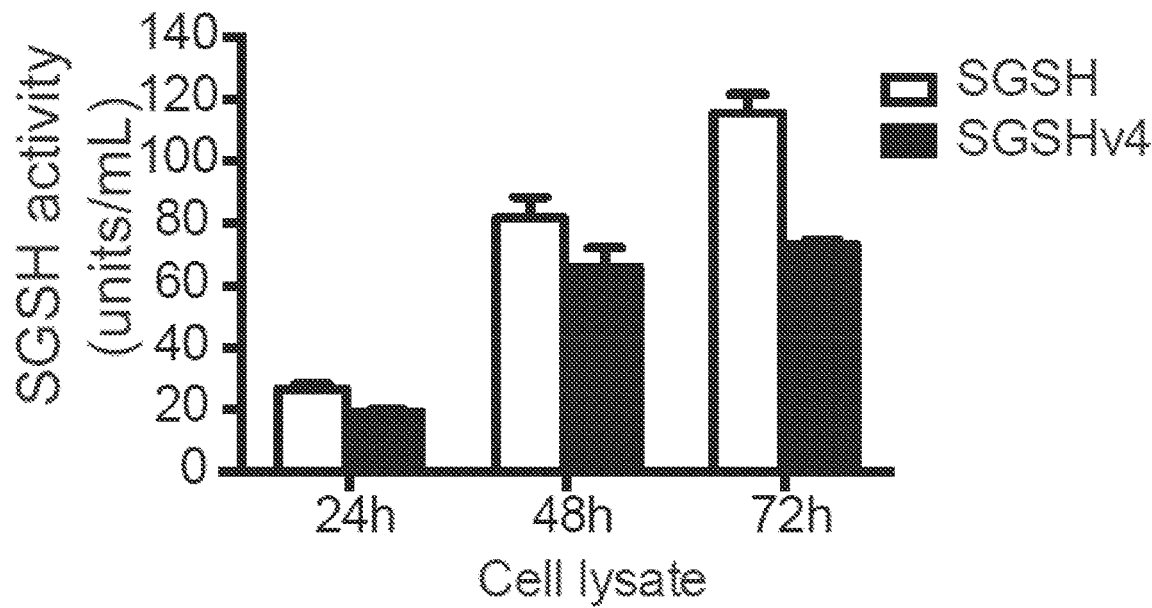
FIG. 5B shows SGSHv4 properties (cell lysate).
Figure 6A:
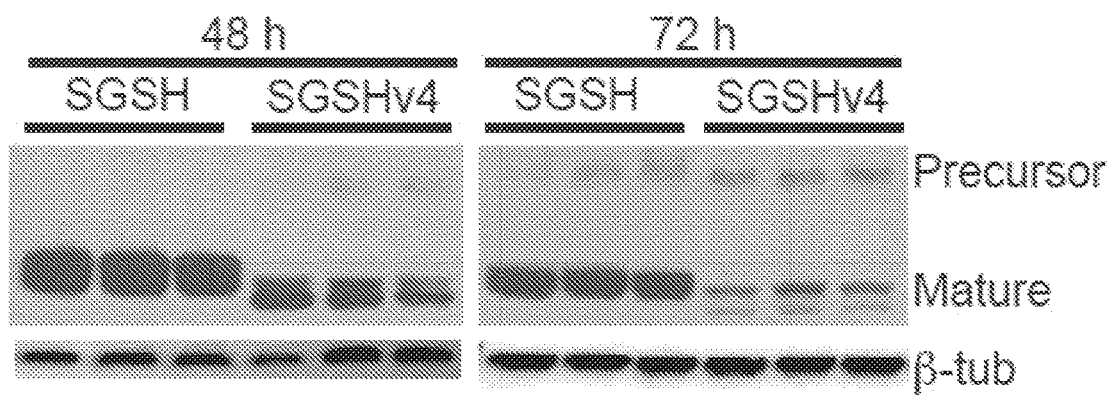
FIG. 6A shows SGSH expression in cell lysate.
Figure 6B:
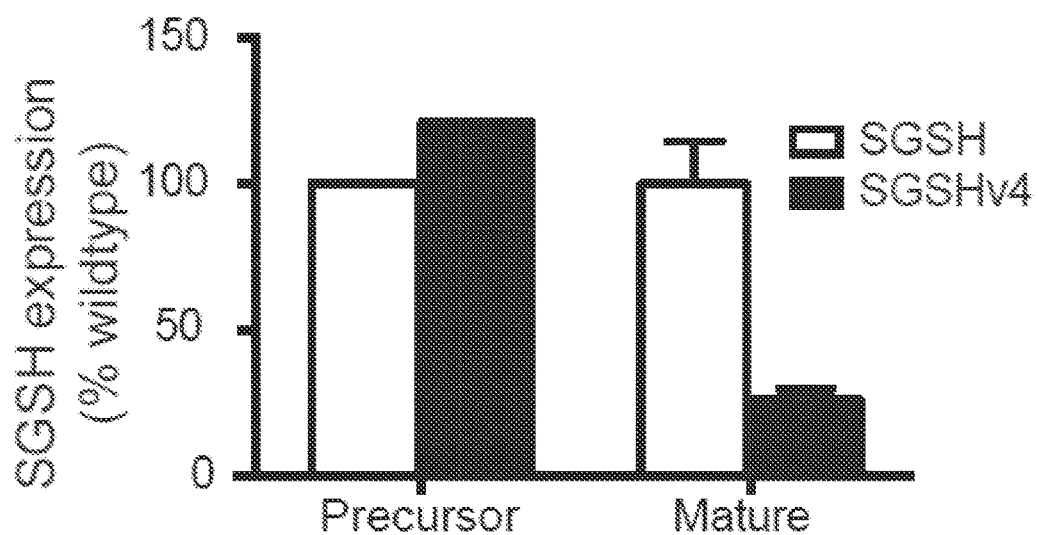
FIG. 6B shows quantification of SGSH expression.
Figure 6C:
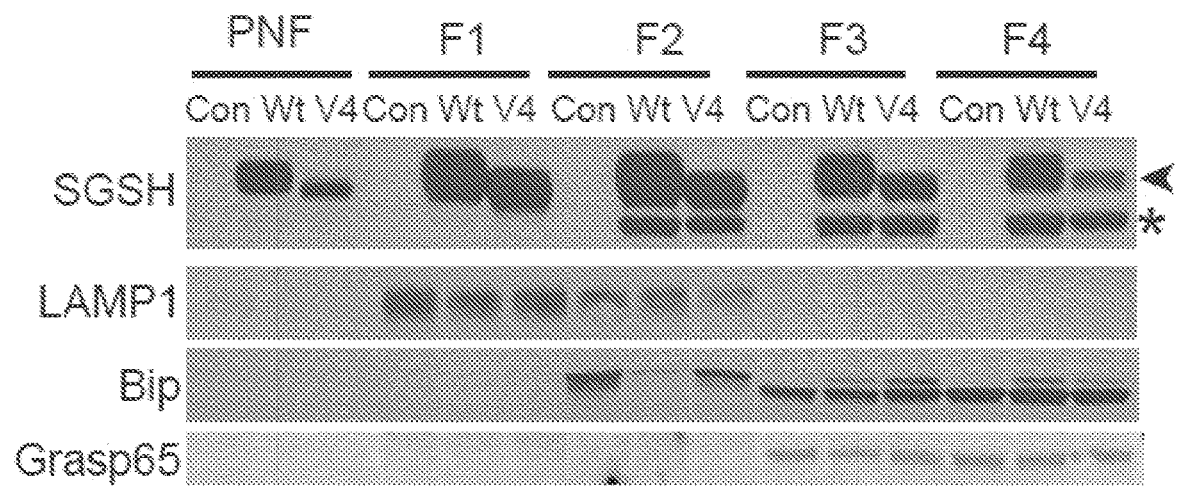
FIG. 6C shows a representative western blot (of four biological replicates) indicating SGSH and SGSHv4 protein levels in the F1, F2, F3 and F4 fractions isolated after gradient centrifugation. LAMP1, Bip, and Grasp 65 were used to identify enrichment of lysosomal, ER, and Golgi markers, respectively. Asterisk (*) indicates unglycosylated SGSH, arrowhead indicates glycosylated SGSH; PNF is the post-nuclear fraction.

HEK 293 cells were transfected with plasmids expressing wildtype or SGSHv4, and enzyme activity and protein levels in media and cell lysates monitored 24, 48 and 72 hours later to monitor enzyme secretion temporally. Cells transfected with SGSHv4 variant-expressing plasmids more efficiently secreted SGSH than those transfected with plasmids expressing the wildtype enzyme at all times. By 24 h there was nearly four times more enzyme in the media of SGSHv4-transfected cells compared to cells transfected with wildtype SGSH expression vectors (FIG. 5A). Conversely, cellular levels of SGSH activity were lower for SGSHv4-vs. wildtype SGSH-expressing cells at all time points (FIG. 5B). Western blots of cell lysates showed reduced levels of precursor SGSH in SGSHv4-expressing cells as well (FIGS. 6A, 6B), supporting the notion that more of the precursor is secreted vs. retained and processed into mature enzyme (as occurs with the wildtype SGSH expression vector). The lower molecular weight of SGSHv4 in both precursor and mature forms is presumably due to reduced phosphorylation levels as a result of the loss of the M6P site.

SGSHv4 Uptake is M6PR Independent

Figure 7:
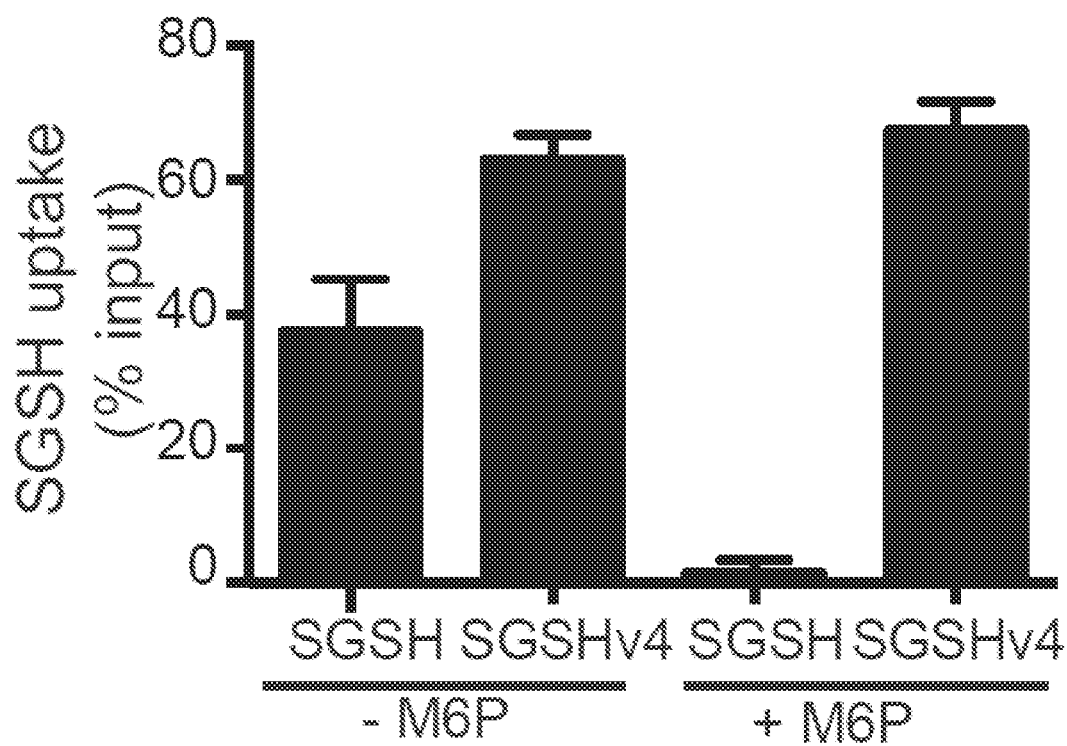
FIG. 7 shows that SGSHv4 has M6PR-Independent uptake.
Figure 8A:
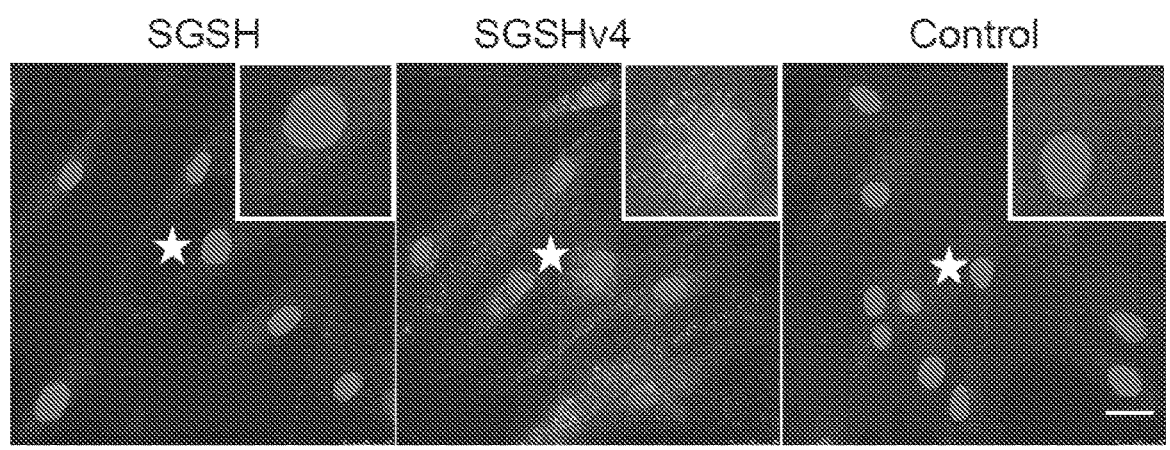
FIG. 8A shows that SGSHv4 is fully processed after uptake (SGSH immunohistology).
Figure 8B:
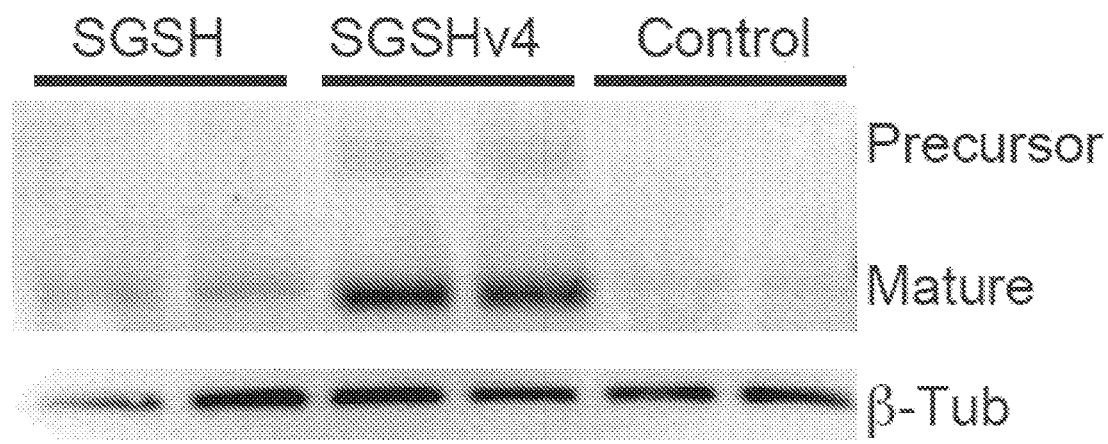
FIG. 8B shows that SGSHv4 is fully processed after uptake (SGSH expression).

The underlying principal for cross correction by gene therapy requires that the enzyme is effectively secreted from over-expressing (transduced) cells, and also that the secreted enzyme can be endocytosed (taken up) by nontransduced cells. As such, the uptake of wildtype and SGSHv4 in MPS IIIA patient fibroblasts was analyzed. Conditioned media from HEK 293 cells expressing wildtype SGSH or SGSHv4 was applied to patient fibroblasts for 6 hours, and then cells collected and activity in cell lysates evaluated. Surprisingly, the SGSHv4-expressed product, N264Q, was more efficiently taken up by patient fibroblasts compared to wildtype SGSH, with >60% of the input of SGSH N264Q entering the cells, vs. <40% for the wildtype SGSH (FIG. 7). Moreover, in the presence of 10 mM M6P, uptake of wildtype SGSH was blocked, but not N264Q (FIG. 7). Importantly, both wildtype and N264Q SGSH are processed to the mature enzyme once internalized, supporting lysosomal delivery (FIGS. 8A, 8B).

AAV.SGSHv4 has improved therapeutic properties in vivo.

Figure 9:
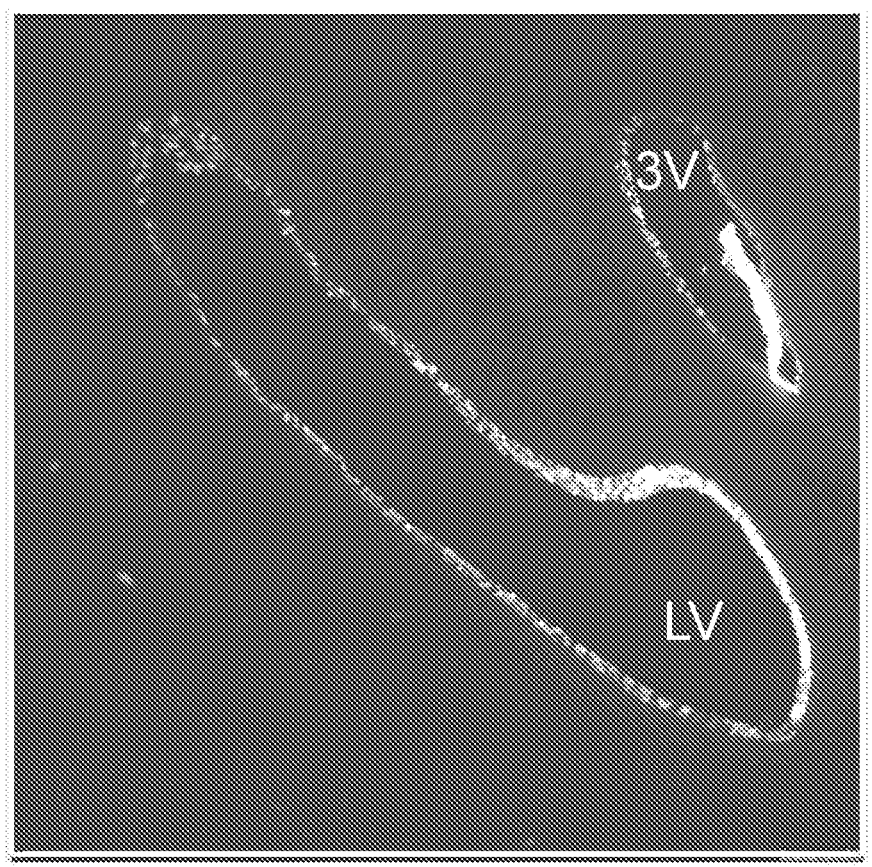
FIG. 9 shows SGSHv4 Gene Therapy in MPSIIIA Mice and that AAV4 targets mouse ependymal.
Figure 10:
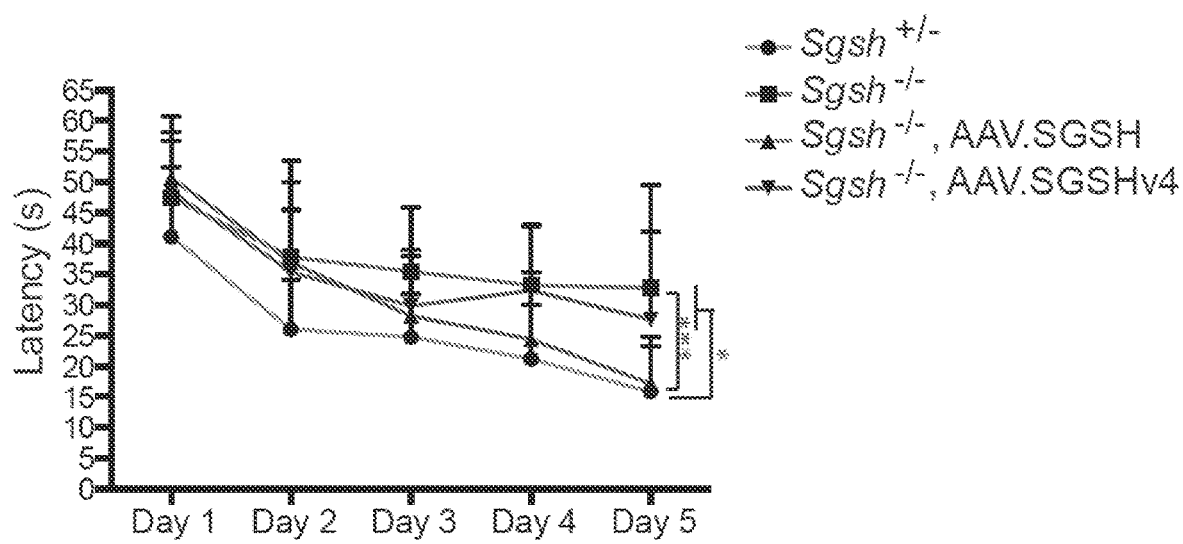
FIG. 10 shows AAV.SGSHv4 impacts disease readouts through Morris Water Maze:
acquisition phase.
Figure 11A:
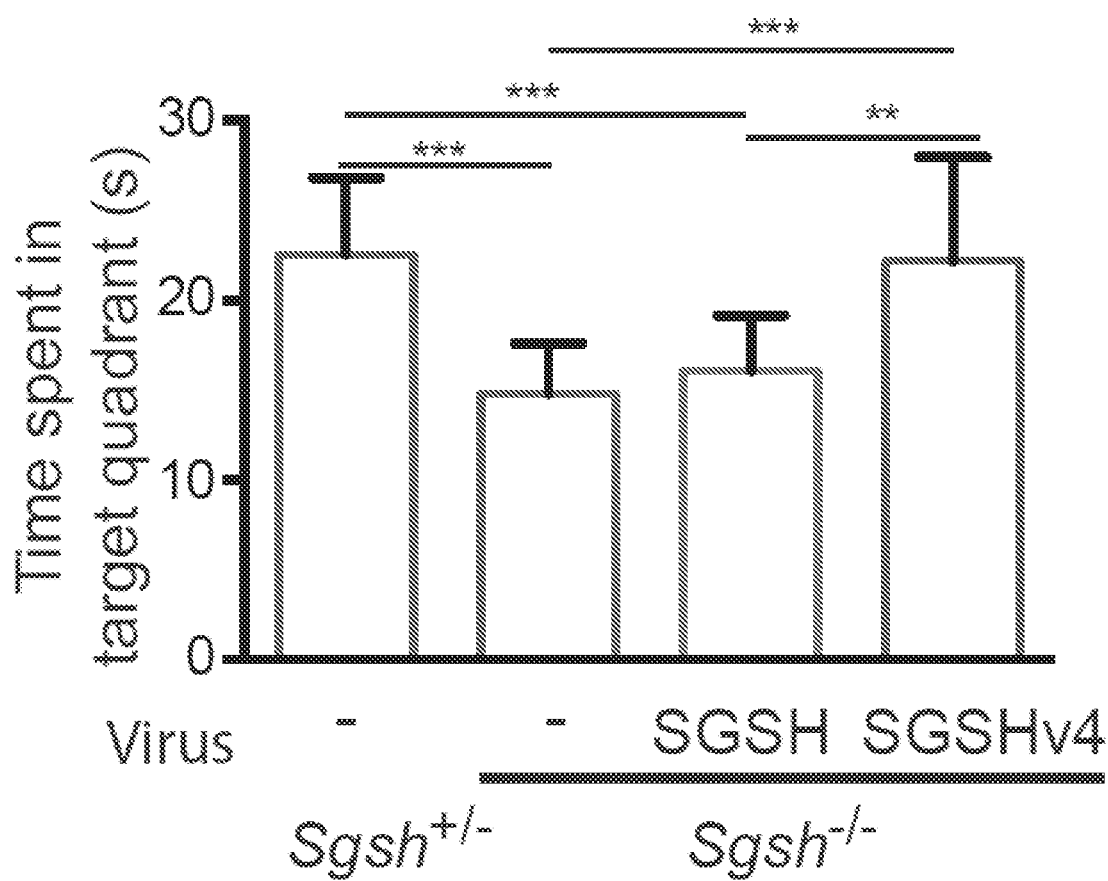
FIG. 11A shows that SGSHv4 improves cognitive deficits (time in target quadrant).
Figure 11B:
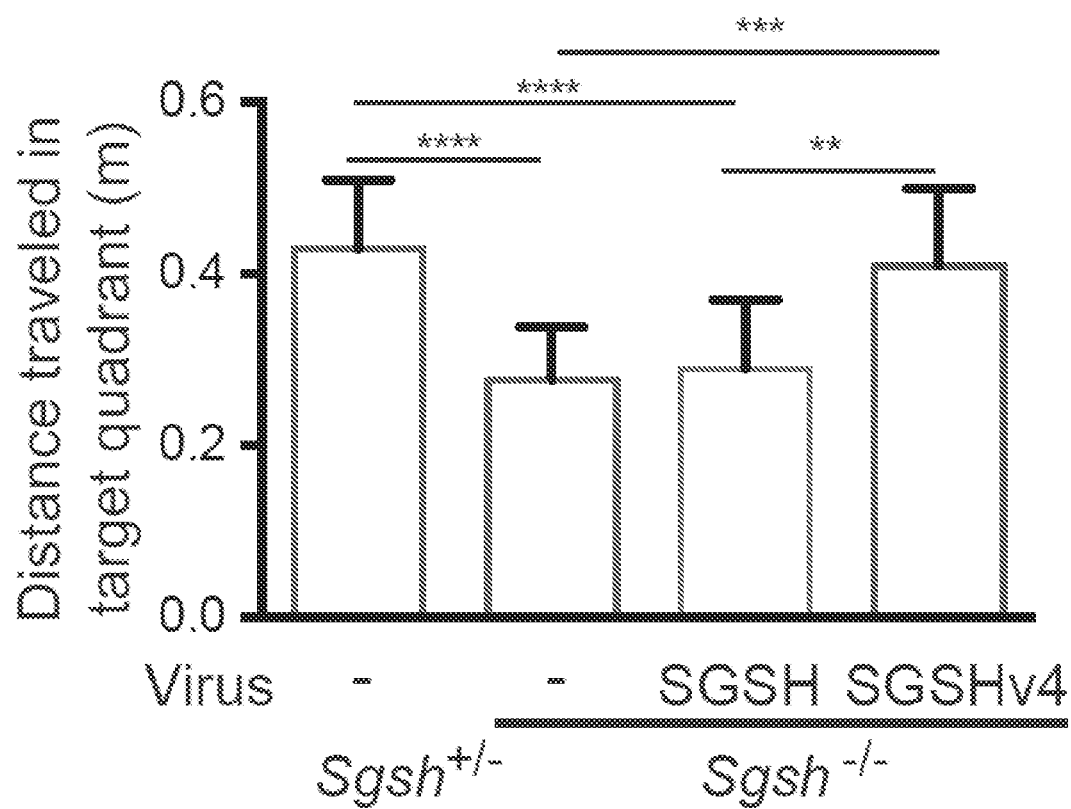
FIG. 11B shows that SGSHv4 improves cognitive deficits (distance in target quadrant).

To compare SGSHv4 to SGSH in vivo, MPS IIIA model mice were injected intraventricularly with AAV4 vectors encoding the different transgenes (AAV.SGSH and AAV.SGSHv4), at the same dose; AAV4 in mice targets ependymal cell exclusively (FIG. 9) (Davidson et al. PNAS USA 97:3428-3432 (2000); Liu, et al. J. Neurosci. 25:9321-9327 (2005)). The mice were analyzed using the Morris water maze for behavioral performance, with spatial learning evaluated by the latency to find the invisible platform (FIG. 10). In AAV.SGSHv4-treated MPS IIIA mice, the latency on day 5 was equivalent to normal, heterozygous littermates, and both groups performed significantly better than untreated disease mice. In contrast, AAV.SGSH-treated mice were similar to untreated disease mice (FIG. 10). MPS IIIA mice treated with AAV.SGSHv4 also performed similar to their heterozygous littermates when assessing the time spent and distance traveled in the target quadrant, while MPS IIIA mice treated with AAV.SGSH behaved similar to untreated disease mice (FIG. 11A, 11B). The data show that intraventricular injection of AAV.SGSHv4, but not AAV.SGSH, is sufficient to correct spatial learning and memory deficits in MPS IIIA mice.

Elevated SGSH activity and improved secondary lysosomal enzyme levels AAV.SGSHv4 treatment.

Figure 12:
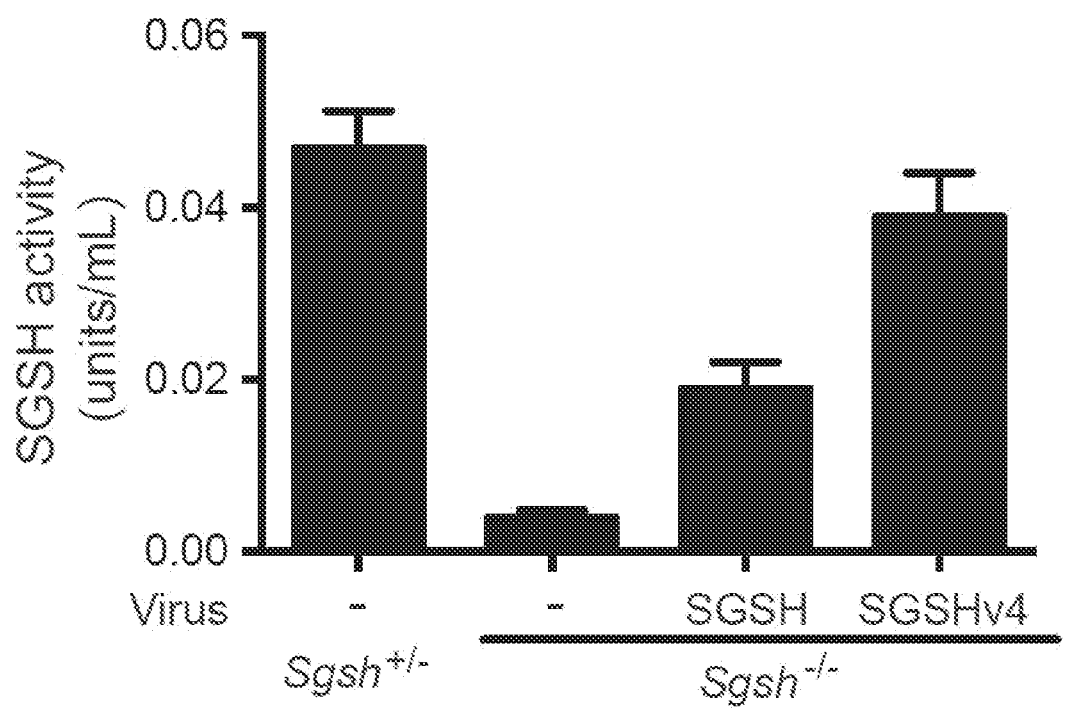
FIG. 12 shows SGSH Activity in CSF.
Figure 13:
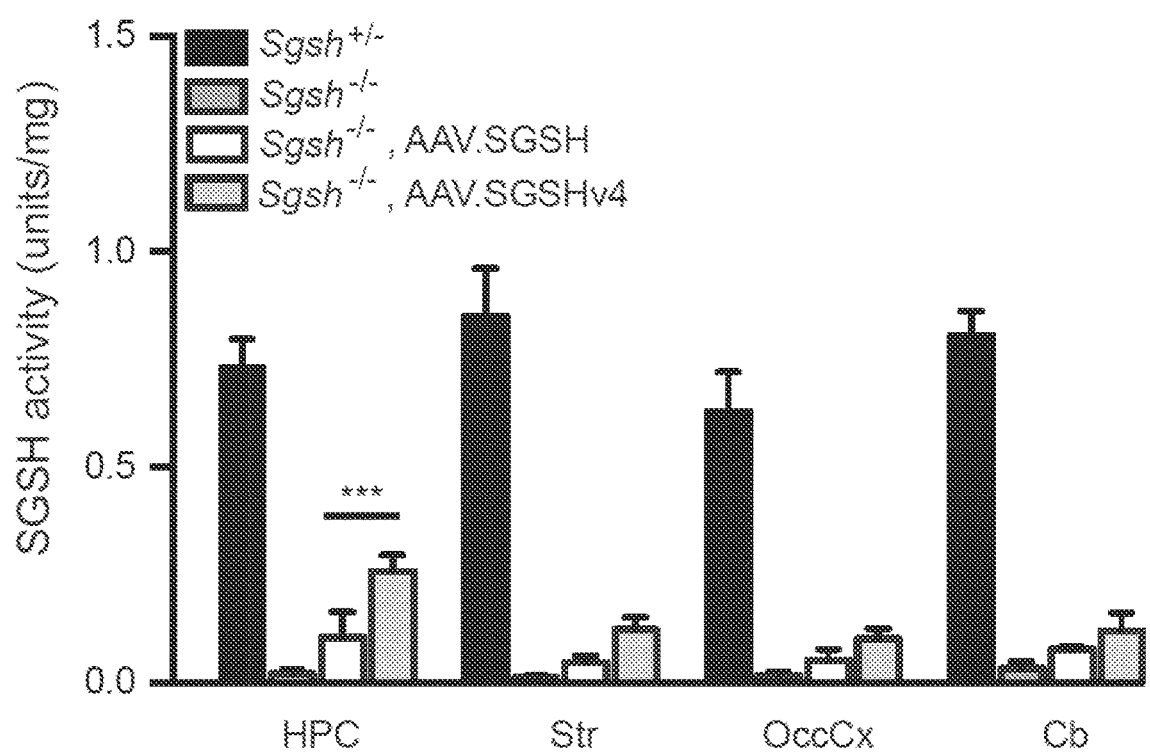
FIG. 13 shows SGSH activity in brain.

SGSH activity in the CSF of AAV.SGSHv4 treated mice reached 80% of heterozygous levels, which was approximately twice that of AAV4.SGSH treated mice (FIG. 12). To evaluate the extent of diffusion, samples from the hippocampus, striatum, occipital cortex and cerebellum were dissected and enzyme activity assessed. Untreated MPS IIIA tissues have ~1-4% of heterozygous levels. MPS IIIA mice treated with AAV.SGSHv4 or AAV.SGSH had increased SGSH activity compared to untreated MPS IIIA mice, however brain regions from AAV.SGSHv4 treated mice were approximately twice those of tissues from AAV.SGSH treated mice. SGSH activity in AAV.SGSHv4 treated mice were 35%, 14.5%, 16% and 14% of heterozygous levels in hippocampus, striatum, occipital cortex and cerebellum, respectively (FIG. 13).

Figure 14:
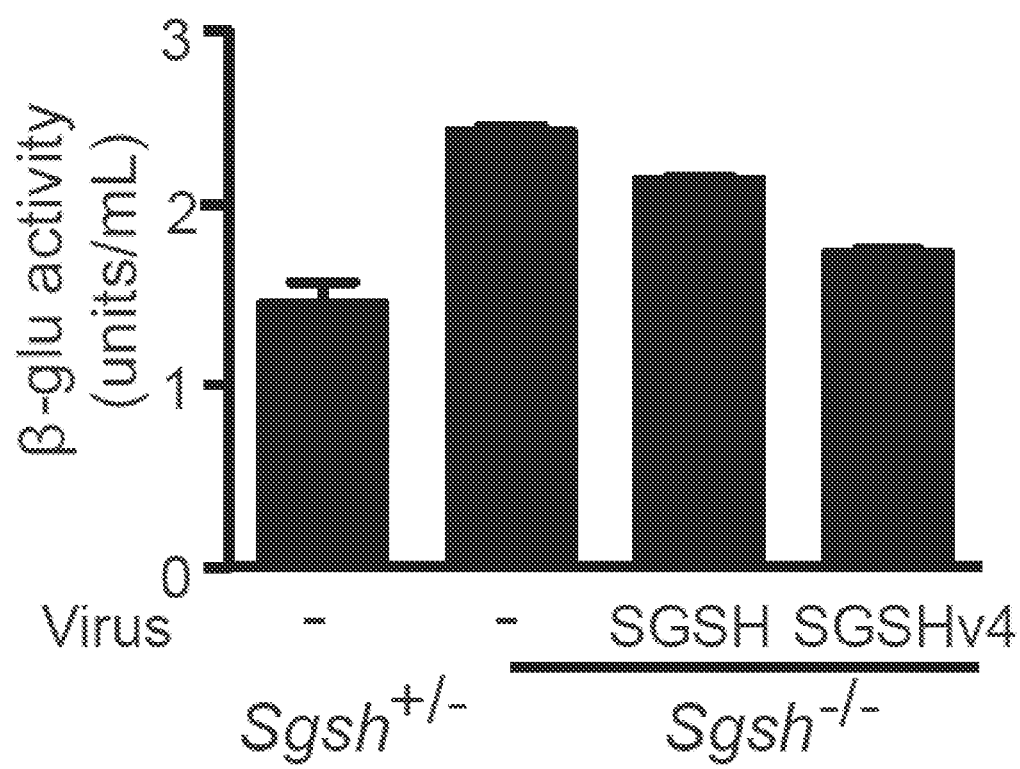
FIG. 14 shows the AAV.SGSHv4 Impact on Secondary Enzymes through β-glucuronidase (β-glu) activity in CSF.
Figure 15:
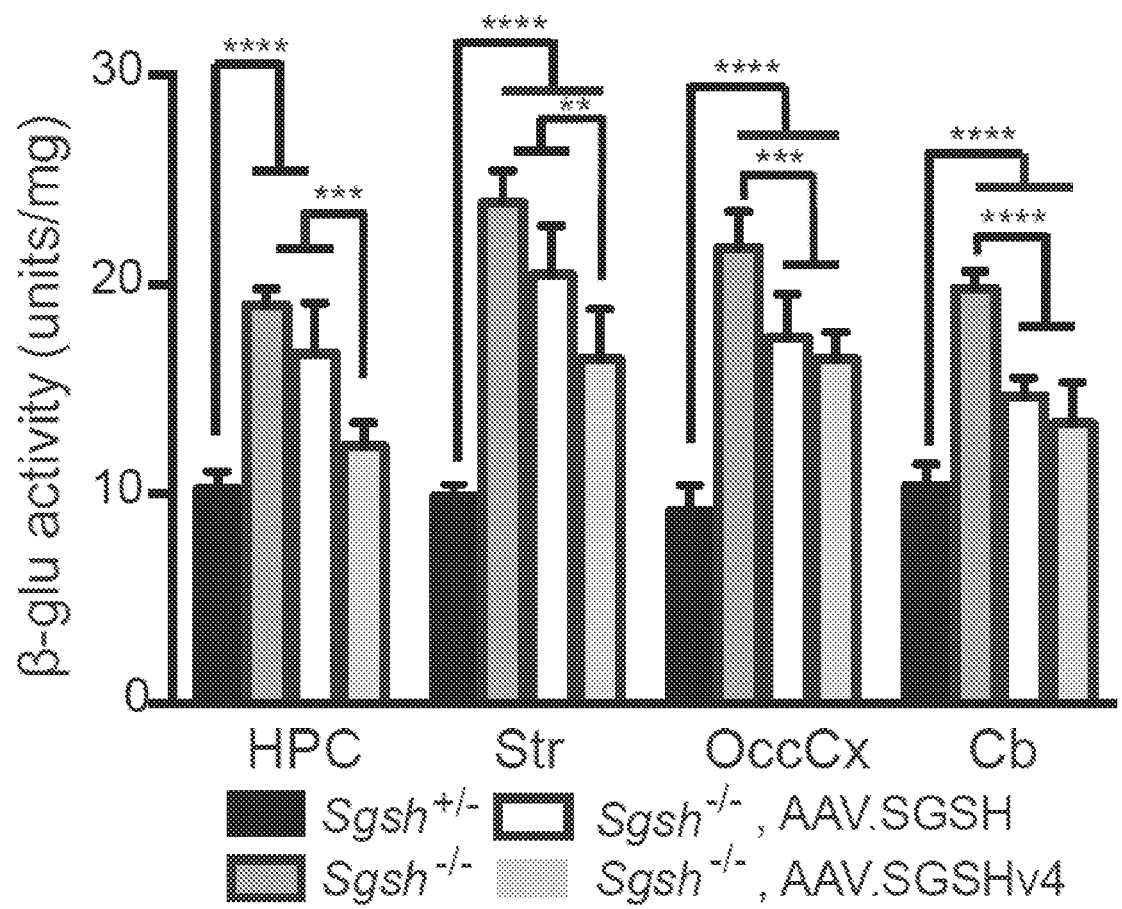
FIG. 15 shows β-glu activity in brain.
Figure 16A:
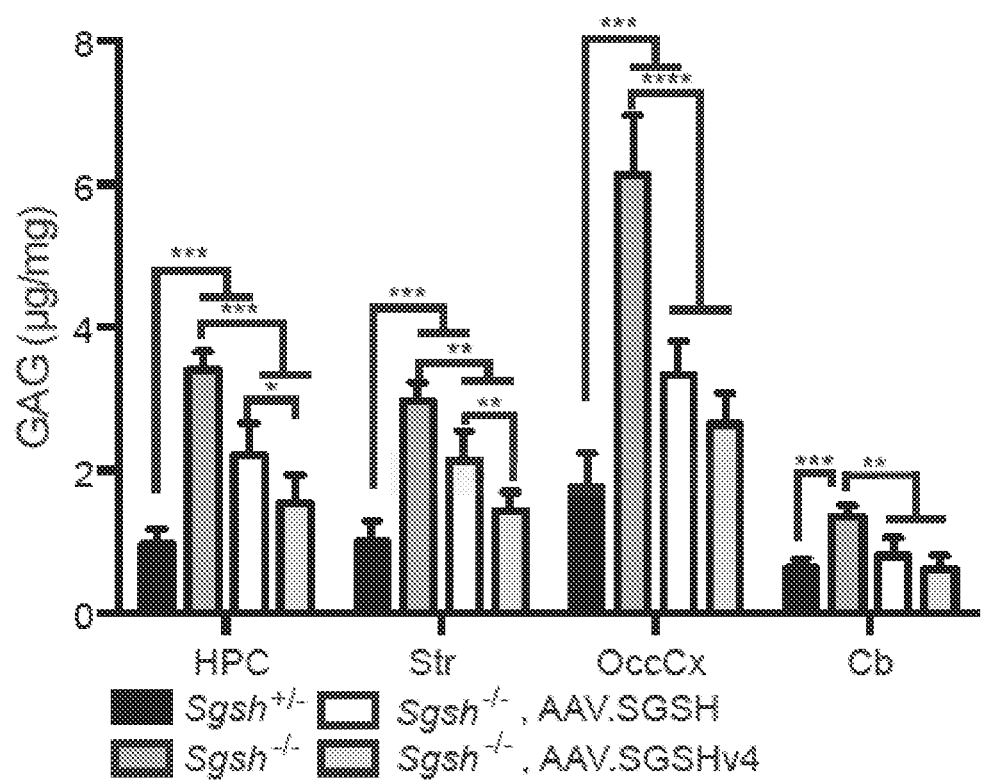
FIG. 16A shows quantification of GAG in parenchyma from tissues harvested contralateral to the injection site: hippocampus (HPC), striatum (Str), occipital cortex (OccCx), and cerebellum (Cb). n=4-6. Data represent mean±SD. $*p<0.05$; $p<0.01$, $*p<0.001$; $****p<0.0001$. One-way ANOVA followed by Tukey's post hoc test.
Figure 16B:
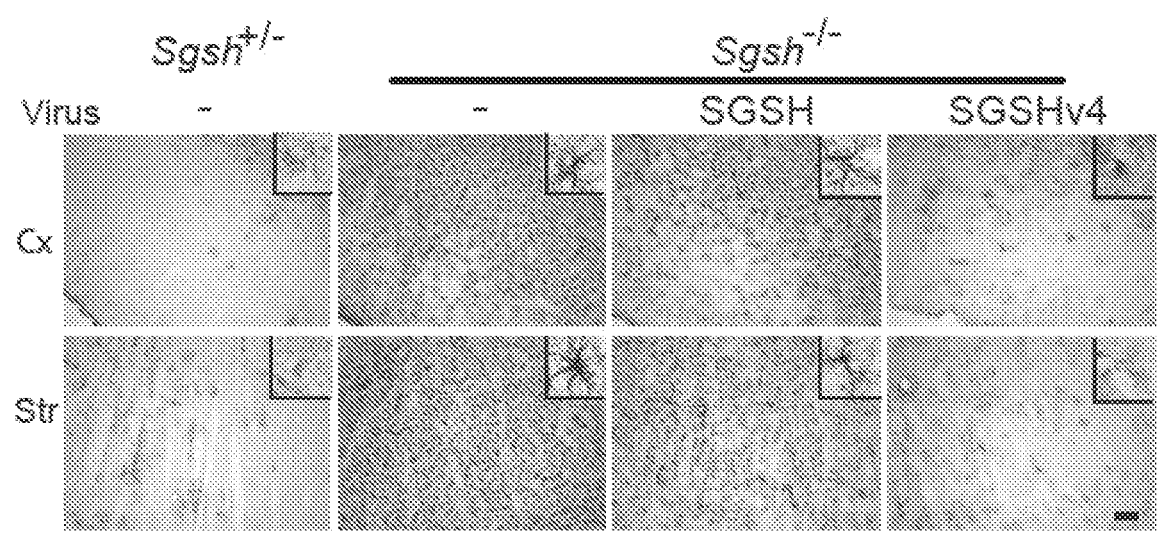
FIG. 16B shows glial astrocytosis measured by immunoreactivity for GFAP in sections collected from hemispheres unilateral to the injection site. Representative photomicrographs are from the cortex (Cx) and striatum (Str); n=3 mice per group, three sections/mouse. Scale bar, 100 μm. Insets show isolated GFAP-immunoreative glia.
Figure 16C:
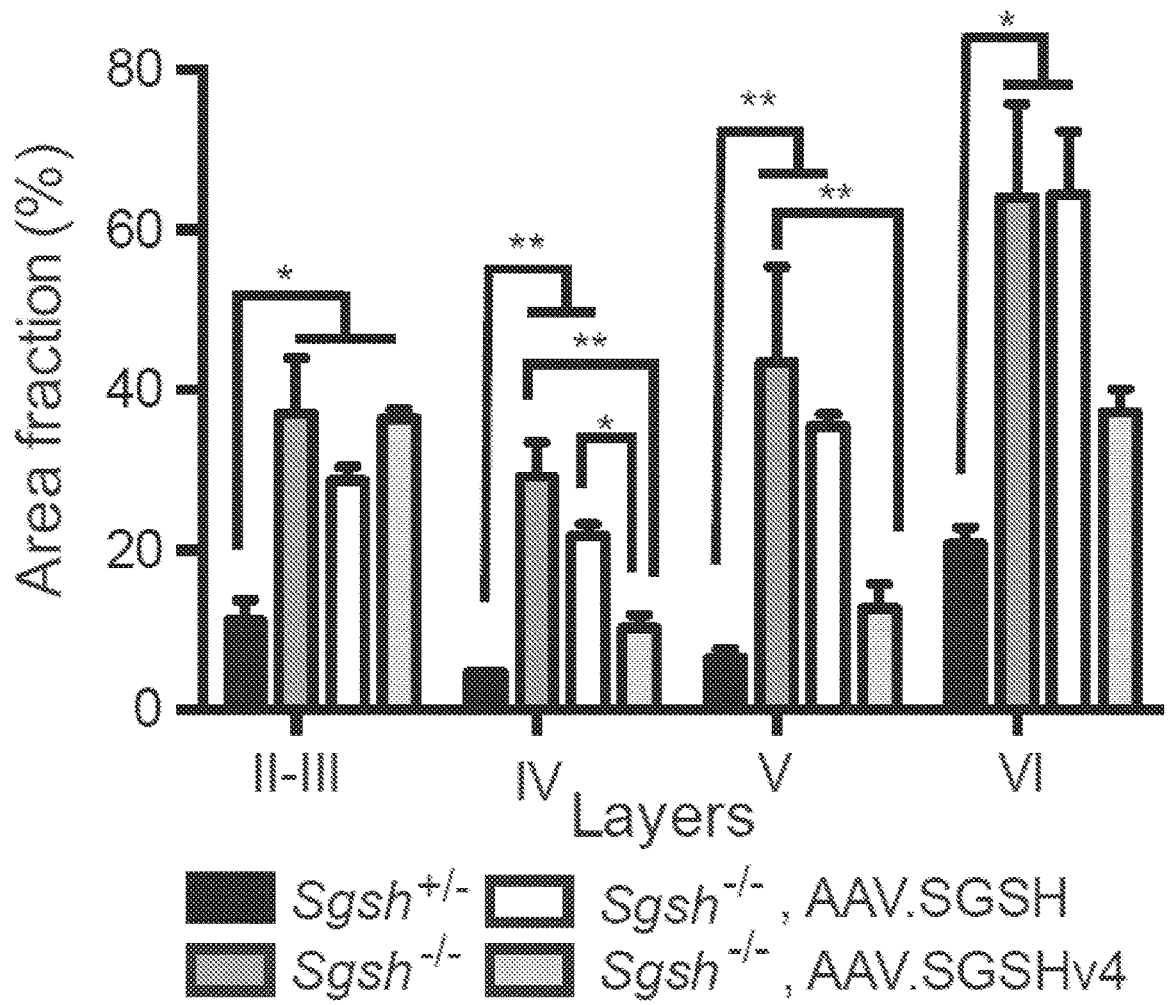
FIGS. 16C and 16D show threshold image analysis measurements of the fraction of total area positive for GFAP immunoreactivity in the cortical layers (C) and striatum (D). Data represent mean±SEM, three mice/group and three sections/mouse. For each section, analyses were done on three random fields (100 μm×100 μm) in the indicated cortical layers and 12 random fields (100 μm×100 μm) in the striatum. $*p<0.05$; $p<0.01$; $**p<0.0001$, Kruskal-Wallis nonparametric test.
Figure 16D:
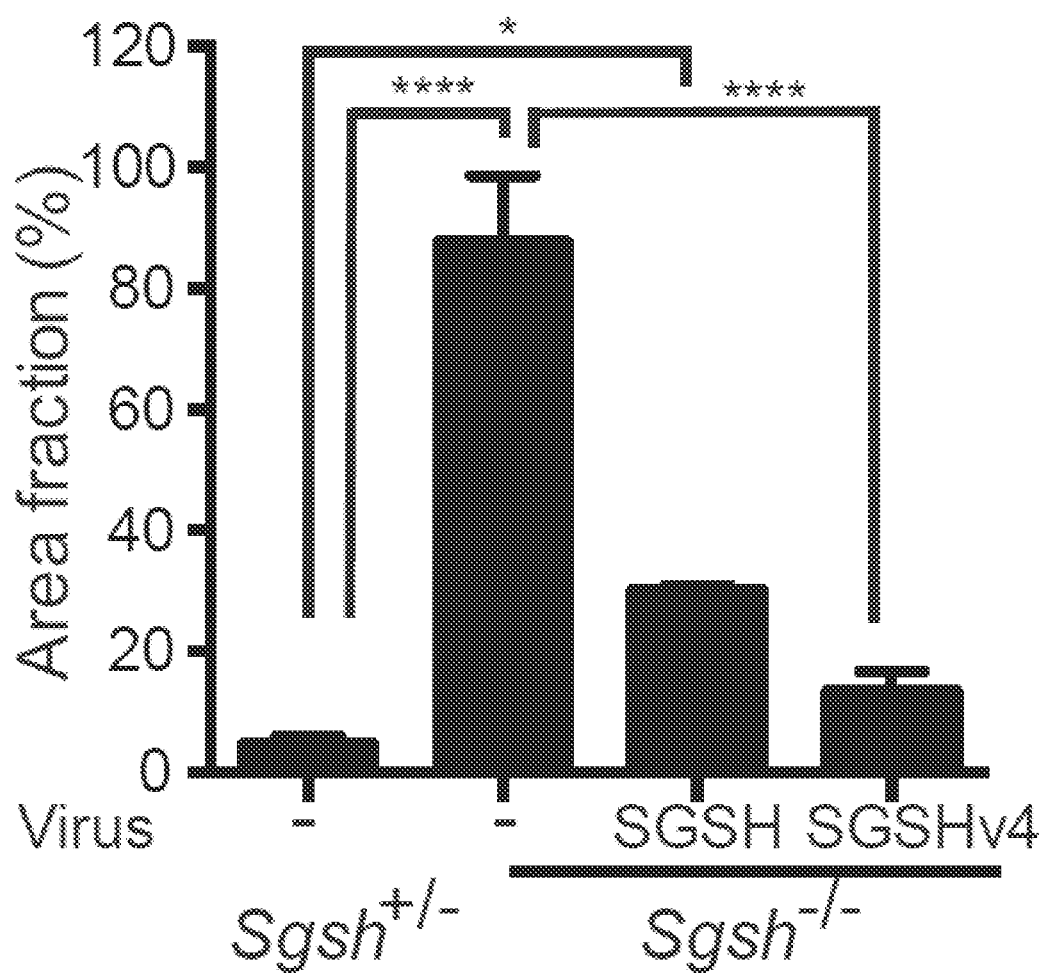

There is significant elevation of β-glu activity in MPS IIIA mice brain, which is secondary to SGSH deficiency (see, e.g., Bhaumik et al. *Glycobiology* 9:1389-1396 (1999)). β-glu activity in the CSF of MPS IIIA mice was 160% of heterozygous levels, which decreased to 120% of heterozygous levels following AAV.SGSHv4 gene transfer, vs. 147% of heterozygous levels after AAV.SGSH treatment (FIG. 14). In brain parenchyma, β-glu activities of MPS IIIA mice were significantly higher than those in heterozygous mice, and were 185%, 242%, 237% and 190% of heterozygous levels in hippocampus, striatum, occipital cortex and cerebellum, respectively. AAV.SGSHv4 decreased β-glu activity levels to 120% and 166% of heterozygous levels in hippocampus and striatum, which is significantly lower than those found in tissue lysates from AAV.SGSH treated mice (163% in hippocampus and 207% in striatum, relative to heterozygous levels). β-glu activities in the occipital cortex and cerebellum of AAV.SGSHv4-treated MPS IIIA mice were decreased compared to untreated MPS IIIA mice, and lower than AAV.SGSH-treated mice, but there was no statistically significant difference from each other (FIG. 15).

Example 3

AAV.SGSHv4 alleviates neuropathology in MPS IIIA mice. Mice (8 wk old) were injected with AAV.SGSH or AAV.HSNv4 into the lateral ventricle. Animals were sacrificed 14 weeks later, and tissues harvested for analysis of impact on neuropathological readouts. The data is shown in FIGS. 16A-16D.

Example 4

Native SGSH is poorly secreted. In contrast, the data show that modified SGSHv4 exhibited increased secretion and cellular uptake by cells. AAV.SGSHv4 also produced elevated enzyme levels in CNS in vivo, and improved penetration in parenchyma. AAV.SGSHv4 was superior to unmodified AAV.SGSH in terms of correcting behavioral deficits in MPS IIIA mouse model. Accordingly, the variant SGSH exemplified herein exhibited one or more of the following attributes: Enhanced cell secretion; improved biodistribution in vivo in the CNS, indicating improved uptake and cross-correction of bystander cells. In addition, phosphorylation levels of beta-glucuronidase, another soluble lysosomal hydrolase, was altered by SGSHv4.

Exemplary wild type or unmodified/non-variant SGSH is set forth as SEQ ID NO:1 below:

```
         10         20         30         40
MSCPVPACCA LLLVLGLCRA RPRNALLLLA DDGGFESGAY 50         60         70         80
NNSAIATPHL DALARRSLLF RNAFTSVSSC SPSRASLLTG 90        100        110        120
LPQHQNGMYG LHQDVHHFNS FDKVRSLPLL LSQAGVRTGI 130        140        150        160
IGKKHVGPET VYPFDFAYTE ENGSVLQVGR NITRIKLLVR 170        180        190        200
KFLQTQDDRP FFLYVAFHDP HRCGHSQPQY GTFCEKFGNG 210        220        230        240
ESGMGRIPDW TPQAYDPLDV LVPYFVPNTP AARADLAAQY 250        260        270        280
TTVGRMDQGV GLVLQELRDA GVLNDTLVIF TSDNGIPFPS 290        300        310        320
GRTNLYWPGT AEPLLVSSPE HPKRWGQVSE AYVSLLDLTP 330        340        350        360
TILDWFSIPY PSYAIFGSKT IHLTGRSLLP ALEAEPLWAT 370        380        390        400
VFGSQSHHEV TMSYPMRSVQ HRHFRLVHNL NFKMPFPIDQ 410        420        430        440
DFYVSPTFQD LLNRTTAGQP TGWYKDLRHY YYRARWELYD 450        460        470        480
RSRDPHETQN LATDPRFAQL LEMLRDQLAK WQWETHDPWV 490        500
CAPDGVLEEK LSPQCQPLHN EL
```

Exemplary CMV enhancer as set forth in SEQ ID NO:2 below:

```
gcgttacataacttacggtaaatggcccgcctggctgaccgcccaacga ccccgcccattgacgtcaataatgacgtatgttcccatagtaacgcca atagggactttccattgacgtcaatgggtggagtatttacggtaaactg cccacttggcagtacatcaagtgtatcatatgccaagtacgccccctat tgacgtcaatgacggtaaatggcccgcctggcattatgcccagtacatg
```

-continued accttatgggactttcctacttggcagtacatctacgtattagtcatcg ctattaccatgg

Exemplary CAG promoter as set forth in SEQ ID NO:3 below:

| Type | Start | End | Description |
|---|---|---|---|
| misc_feature | 1 | 1672 | /note = CAG promoter |
| regulatory | 22 | 327 | /note = CMV enhancer |
| promoter | 328 | 605 | /note = chicken beta-actin promoter |
| intron | 607 | 1624 | /note = chimeric intron /note = chimera between introns from chicken beta-actin and rabbit beta-globin |
| regulatory | 1528 | 1672 | /note = predicted transcription factor sites |
| regulatory | 1575 | 1672 | /note = iowa predicted transcription factor binding site |

ATAGCCCATATATGGAGTTCCGCGTTACATAACTTACGGTAAATGGCCC

GCCTGGCTGACCGCCCAACGACCCCCGCCCATTGACGTCAATAATGACG

TATGTTCCCATAGTAACGCCAATAGGGACTTTCCATTGACGTCAATGGG

TGGAGTATTTACGGTAAACTGCCCACTTGGCAGTACATCAAGTGTATCA

TATGCCAAGTACGCCCCCTATTGACGTCAATGACGGTAAATGGCCCGCC

TGGCATTATGCCCAGTACATGACCTTATGGGACTTTCCTACTTGGCAGT

ACATCTACGTATTAGTCATCGCTATTACCATGGTCGAGGTGAGCCCCAC

GTTCTGCTTCACTCTCCCCATCTCCCCCCCCTCCCCACCCCCAATTTTG

TATTTATTTATTTTTTAATTATTTTGTGCAGCGATGGGGGCGGGGGGGG

GGGGGGGGCGCGCGCCAGGCGGGGCGGGGCGGGGCGAGGGGCGGGGCGG

GGCGAGGCGGAGAGGTGCGGCGGCAGCCAATCAGAGCGGCGCGCTCCGA

AAGTTTCCTTTTATGGCGAGGCGGCGGCGGCGGCGGCCCTATAAAAAGC

GAAGCGCGCGGCGGGCGGGGAGTCGCTGCGACGCTGCCTTCGCCCCGTG

CCCCGCTCCGCCGCCGCCTCGCGCCGCCCGCCCCGGCTCTGACTGACCG

CGTTACTCCCACAGGTGAGCGGGCGGGACGGCCCTTCTCCTCCGGGCTG

TAATTAGCGCTTGGTTTAATGACGGCTTGTTTCTTTTCTGTGGCTGCGT

GAAAGCCTTGAGGGGCTCCGGGAGGGCCCTTTGTGCGGGGGGAGCGGCT

CGGGGGGTGCGTGCGTGTGTGTGCGTGGGGAGCGCCGCGTGCGGCTC

CGCGCTGCCCGGCGGCTGTGAGCGCTGCGGGCGCGGCGCGGGGCTTTGT

GCGCTCCGCAGTGTGCGCGAGGGGAGCGCGGCCGGGGCGGTGCCCCGC

GGTGCGGGGGGGCTGCGAGGGGAACAAAGGCTGCGTGCGGGGTGTGTG

CGTGGGGGGGTGAGCAGGGGGTGTGGGCGCGTCGGTCGGGCTGCAACCC

CCCCTGCACCCCCCTCCCCGAGTTGCTGAGCACGGCCCGGCTTCGGGTG

-continued

CGGGGCTCCGTACGGGGCGTGGCGCGGGGCTCGCCGTGCCGGGCGGGGG

GTGGCGGCAGGTGGGGGTGCCGGGCGGGGCGGGGCCGCCTCGGGCCGGG

GAGGGCTCGGGGGAGGGGCGCGGCGGCCCCCGGAGCGCCGGCGGCTGTC

GAGGCGCGGCGAGCCGCAGCCATTGCCTTTTATGGTAATCGTGCGAGAG

GGCGCAGGGACTTCCTTTGTCCCAAATCTGTGCGGAGCCGAAATCTGGG

AGGCGCCGCCGCACCCCCTCTAGCGGGCGCGGGGCGAAGCGGTGCGGCG

CCGGCAGGAAGGAAATGGGCGGGGAGGGCCTTCGTGCGTCGCCGCGCCG

CCGTCCCCTTCTCCCTCTCCAGCCTCGGGGCTGTCCGCGGGGGGACGGC

TGCCTTCGGGGGGGACGGGGCAGGGCGGGGTTCGGCTTCTGGCGTGTGA

CCGGCGGCTCTAGAGCCTCTGCTAACCATGTTCATGCCTTCTTCTTTTT

CCTACAGCTCCTGGGCAACGTGCTGGTTATTGTGCTGTCTCATCATTTT

GGCAAA

REFERENCES

Katz, M. L. et al. AAV gene transfer delays disease onset in a TPP1-deficient canine model of the late infantile form of Batten disease (2015) *Science Translational Medicine* 7, 313ra180.

Liu, G., Martins, I., Wemmie, J. A., Chiorini, J. A. & Davidson, B. L. Functional correction of CNS phenotypes in a lysosomal storage disease model using adeno-associated virus type 4 vectors. (2005) *The Journal of Neuroscience: the Official Journal of the Society for Neuroscience* 25, 9321-9327.

Davidson, B. L. et al. Recombinant adeno-associated virus type 2, 4, and 5 vectors: transduction of variant cell types and regions in the mammalian central nervous system (2000) *Proceedings of the National Academy of Sciences of the United States of America* 97, 3428-3432.

Bhaumik, M. et al. A mouse model for mucopolysaccharidosis type III A (Sanfilippo syndrome) (1999) *Glycobiology* 9, 1389-1396.

Karpova, E. A. et al. A fluorimetric enzyme assay for the diagnosis of Sanfilippo disease type A (MPS IIIA) (1996) *Journal of Inherited Metabolic Disease* 19, 278-285.

Tian, Y., Sohar, I., Taylor, J. W. & Lobel, P. Determination of the substrate specificity of tripeptidyl-peptidase I using combinatorial peptide libraries and development of improved fluorogenic substrates (2006) *The Journal of Biological Chemistry* 281, 6559-6572.

Bhattacharyya, R., Gliddon, B., Beccari, T., Hopwood, J. J. & Stanley, P. A novel missense mutation in lysosomal sulfamidase is the basis of MPS III A in a spontaneous mouse mutant (2001) *Glycobiology* 11, 99-103.

Vorhees, C. V. & Williams, M. T. Morris water maze: procedures for assessing spatial and related forms of learning and memory (2006) *Nature Protocols* 1, 848-858.

What is claimed:

1. A method of delivering sulfamidase (SGSH) to the central nervous system of a mammal, comprising administering to the mammal's central nervous system (CNS) a recombinant adeno-associated virus (rAAV) particle comprising a nucleic acid encoding a sulfamidase (SGSH) variant that is at least 90% identical to SEQ ID NO: 1 and has an amino acid substitution at position 264 of SEQ ID NO: 1, wherein the rAAV particle is injected at 1-5 locations in the brain effective to transduce cells that contact the cerebrospinal fluid (CSF) of the mammal such that the cells express and secrete the sulfamidase (SGSH) variant in the mammal.

2. A method of delivering sulfamidase (SGSH) to the central nervous system of a mammal, comprising administering to the mammal's brain parenchyma, subarachnoid space and/or intrathecal space a recombinant adeno-associated virus (rAAV) particle comprising a nucleic acid encoding a sulfamidase (SGSH) variant that is at least 90% identical to SEQ ID NO:1 and has an amino acid substitution at position 264 of SEQ ID NO:1, wherein the rAAV particle is injected at 1-5 locations in the brain in a manner effective to transduce brain parenchyma cells or cells that contact the cerebrospinal fluid (CSF) of the mammal such that the cells express and secrete the SGSH variant in the mammal.

3. The method of any one of claims 1 and 2, wherein the rAAV particle is administered in single or multiple doses to any of the mammal's cisterna magna, intraventricular space, brain ventricle, subarachnoid space, intrathecal space and/or ependyma.

4. A method of delivering sulfamidase (SGSH) to the central nervous system of a mammal, comprising administering to the mammal's central nervous system (CNS) a recombinant adeno-associated virus (rAAV) particle comprising a nucleic acid encoding a sulfamidase (SGSH) variant that is at least 90% identical to SEQ ID NO: 1 and has an amino acid substitution at position 264 of SEQ ID NO: 1, wherein the rAAV particle is injected at a single location in the brain effective to transduce cells that contact the cerebrospinal fluid (CSF) of the mammal such that the cells express and secrete the sulfamidase (SGSH) variant in the mammal.

5. A method of delivering sulfamidase (SGSH) to the central nervous system of a mammal, comprising administering to the mammal's brain parenchyma, subarachnoid space and/or intrathecal space a recombinant adeno-associated virus (rAAV) particle comprising a nucleic acid encoding a sulfamidase (SGSH) variant that is at least 90% identical to SEQ ID NO:1 and has an amino acid substitution at position 264 of SEQ ID NO:1, wherein the rAAV particle is injected at a single location in the brain in a manner effective to transduce brain parenchyma cells or cells that contact the cerebrospinal fluid (CSF) of the mammal such that the cells express and secrete the SGSH variant in the mammal.

6. The method of any one of claims 1, 2, 4 and 5, wherein the administration is to the brain ventricle.

7. The method of any one of claims 1, 2, 4 and 5, wherein the delivering or administering comprises intraventricular injection and/or intraparenchymal injection.

8. The method of any one of claims 1, 2, 4 and 5, comprising administering or delivering the rAAV particle to the mammal's brain ventricle, subarachnoid space and/or intrathecal space.

9. The method of any one of claims 1, 2, 4 and 5, wherein the brain ventricle comprises a lateral ventricle.

10. The method of any one of claims 1, 2, 4 and 5, wherein the rAAV particle is administered to the: rostral lateral ventricle; and/or caudal lateral ventricle; and/or right lateral ventricle; and/or left lateral ventricle; and/or right rostral lateral ventricle; and/or left rostral lateral ventricle; and/or right caudal lateral ventricle; and/or left caudal lateral ventricle.

11. A method of delivering sulfamidase (SGSH) to the central nervous system of a mammal, comprising administering to the mammal's central nervous system (CNS) a recombinant adeno-associated virus (rAAV) particle comprising a nucleic acid encoding a sulfamidase (SGSH) variant that is at least 90% identical to SEQ ID NO: 1 and has an amino acid substitution at position 264 of SEQ ID NO: 1, wherein the rAAV particle is administered to the: rostral lateral ventricle; and/or caudal lateral ventricle; and/or right lateral ventricle; and/or left lateral ventricle; and/or right rostral lateral ventricle; and/or left rostral lateral ventricle; and/or right caudal lateral ventricle; and/or left caudal lateral ventricle effective to transduce cells that contact the cerebrospinal fluid (CSF) of the mammal such that the cells express and secrete the sulfamidase (SGSH) variant in the mammal.

12. A method of delivering sulfamidase (SGSH) to the central nervous system of a mammal, comprising administering to the mammal's brain parenchyma, subarachnoid space and/or intrathecal space a recombinant adeno-associated virus (rAAV) particle comprising a nucleic acid encoding a sulfamidase (SGSH) variant that is at least 90% identical to SEQ ID NO:1 and has an amino acid substitution at position 264 of SEQ ID NO:1, wherein the rAAV particle is administered to the: rostral lateral ventricle; and/or caudal lateral ventricle; and/or right lateral ventricle; and/or left lateral ventricle; and/or right rostral lateral ventricle; and/or left rostral lateral ventricle; and/or right caudal lateral ventricle; and/or left caudal lateral ventricle in a manner effective to transduce brain parenchyma cells or cells that contact the cerebrospinal fluid (CSF) of the mammal such that the cells express and secrete the SGSH variant in the mammal.

13. The method of any one of claims 1, 2, 4, 5, 11 and 12, wherein the rAAV particle comprises an AAV capsid protein and the nucleic acid is inserted between a pair of AAV inverted terminal repeats (ITRs).

14. The method of claim 13, wherein the AAV capsid protein a) is a VP1, VP2 or VP3 capsid protein derived from or selected from the group consisting of AAV1, AAV2, AAV3, AAV4, AAV5, AAV6, AAV7, AAV8, AAV9, AAV10, AAV11, AAV12, AAV-rh74, AAV-rh10 and AAV-218 VP1, VP2 and VP3 capsid proteins; or (b) is a VP1, VP2 or VP3 capsid protein having 70% or more identity to an AAV1, AAV2, AAV3, AAV4, AAV5, AAV6, AAV7, AAV8, AAV9, AAV10, AAV11, AAV12, AAV-rh74, AAV-Rh10, or AAV-218 VP1, VP2 and VP3 capsid sequence.

15. The method of claim 13, wherein the one or more of the pair of ITRs a) is derived from, comprises or consists of an AAV1, AAV2, AAV3, AAV4, AAV5, AAV6, AAV7, AAV8, AAV9, AAV10, AAV11, AAV12, AAV-rh74, AAV-rh10 or AAV-218 ITR; or b) is an ITR having 70% or more identity to an AAV1, AAV2, AAV3, AAV4, AAV5, AAV6, AAV7, AAV8, AAV9, AAV10, AAV11, AAV12, AAV-rh74, or AAV-Rh10 ITR sequence.

16. The method of claim 13, wherein a plurality of rAAV particles are administered.

17. The method of claim 16, wherein the rAAV particles are administered at a dose of about $1\times10^6$ to about $1\times10^{18}$ vg/kg.

18. The method of claim 16, wherein the rAAV particles are administered at a dose from about $1\times10^7$-$1\times10^{17}$, about $1\times10^8$-$1\times10^{16}$, about $1\times10^9$-$1\times10^{15}$, about $1\times10^{10}$-$1\times10^{14}$, about $1\times10^{10}$-$1\times10^{13}$, about $1\times10^{10}$-$1\times10^{12}$, about $1\times10^{10}$-$1\times10^{11}$, about $1\times10^{11}$-$1\times10^{12}$, about $1\times10^{12}$-$1\times10^{13}$, or about $1\times10^{13}$-$1\times10^{14}$ vector genomes per kilogram (vg/kg) of the mammal.

19. The method of claim 16, wherein the rAAV particles are administered at a dose of about 0.5-4 ml of $1\times10^6$-$1\times10^{16}$ vg/ml.

20. The method of claim 13, further comprising administering a plurality of AAV empty capsids.

21. The method of claim 20, wherein the empty AAV capsids are formulated with the rAAV particles administered to the mammal.

22. The method of claim 20, wherein the AAV empty capsids are administered or formulated with 1.0 to 100-fold excess of rAAV vector particles.

23. The method of claim 20, wherein the AAV empty capsids are administered or formulated with about 1.0 to 100-fold excess of AAV empty capsids to rAAV particles.

24. The method of any one of claims 1, 2, 4, 5, 11 and 12, wherein the nucleic acid further comprises an expression control element.

25. The method of claim 24, wherein the expression control element comprises a promoter.

26. The method of claim 24, wherein the expression control element comprises an enhancer element.

27. The method of claim 24, wherein the expression control element comprises a CMV enhancer, chicken beta actin promoter, CAG promoter and/or a sequence having 80% or more identity to CMV enhancer set forth in SEQ ID NO:2 and/or a sequence having 80% or more identity to CAG promoter set forth in SEQ ID NO:3.

28. The method of any of claims 1, 2, 4, 5, 11 and 12, wherein the nucleic acid further comprises one or more of an intron, a filler polynucleotide sequence and/or poly A signal, or a combination thereof.

29. The method of any one of claims 1, 2, 4, 5, 11 and 12, wherein the cells comprise ependymal cells, pial cells, endothelial cells, brain ventricle cells, meningeal cells, glial cells and/or neurons.

30. The method of any one of claims 1, 2, 4, 5, 11 and 12, wherein the cells secrete the SGSH variant into the CNS of said mammal.

31. The method of any one of claims 1, 2, 4, 5, 11 and 12, wherein the cells secrete the SGSH variant into the CSF of said mammal.

32. The method of claim 31, wherein the ependymal cell, pial cell, endothelial cell, brain ventricle cell, meningeal cell, glial cell and/or neuron expresses the SGSH variant and/or wherein the ependymal cell, pial cell, endothelial cell, brain ventricle cell, meningeal cell, glial cell and/or neuron secretes the SGSH variant into the CSF.

33. The method of any one of claims 1, 2, 4, 5, 11 and 12, wherein the rAAV particle is injected at a single location in the brain.

34. The method of any one of claims 1, 2, 4, 5, 11 and 12, wherein the method increases SGSH variant expression to between about 5-50% of normal SGSH expression.

35. The method of any one of claims 1, 2, 4, 5, 11 and 12, wherein the method increases SGSH variant expression to above 50% of normal SGSH expression.

36. The method of any one of claims 1, 2, 4, 5, 11 and 12, wherein the mammal is a non-rodent mammal.

37. The method of claim 36, wherein the non-rodent mammal is a primate, horse, sheep, goat, pig, or dog.

38. The method of claim 37, wherein the primate is human.

39. The method of claim 38, wherein the human is a child.

40. The method of claim 39, wherein the child is from about 1 to about 8 years of age.

41. The method of claim 36, wherein the non-rodent mammal is a primate.

42. The method of any one of claims 1, 2, 4, 5, 11 and 12, wherein the mammal, primate or human exhibits a loss of or reduced endogenous SGSH expression or function.

43. The method of any one of claims 1, 2, 4, 5, 11 and 12, wherein the mammal, primate or human is homozygous (Sgsh$^{-/-}$) or heterozygous (Sgsh$^{+/-}$) with respect to lost or reduced SGSH expression or function.

44. The method of any one of claims 1, 2, 4, 5, 11 and 12, further comprising administering one or more immunosuppressive agents.

45. The method of claim 44, wherein said immunosuppressive agent is administered prior to or contemporaneously with administration or delivery of said vector.

46. The method of claim 44, wherein the immunosuppressive agent is an anti-inflammatory agent.

47. The method of any one of claims 1, 2, 4, 5, 11 and 12, wherein the SGSH variant is distributed to non-transduced cells in CNS.

48. The method of any one of claims 1, 2, 4, 5, 11 and 12, wherein the SGSH variant is distributed to non-transduced CNS cells by way of cerebrospinal fluid (CSF).

49. The method of any one of claims 1, 2, 4, 5, 11 and 12, wherein the SGSH variant is distributed to non-transduced CNS cells located distal to the transduced cells.

50. The method of any one of claims 1, 2, 4, 5, 11 and 12, wherein the SGSH is taken up by CNS cells.

51. The method of any one of claims 1, 2, 4, 5, 11 and 12, wherein the SGSH variant is at least 95% identical to SEQ ID NO: 1 having an amino acid substitution at position 264.

52. The method of any one of claims 1, 2, 4, 5, 11 and 12, wherein the SGSH variant is at least 90% identical to SEQ ID NO: 1 having an asparagine (N)→glutamine (Q) substitution at position 264.

53. The method of any one of claims 1, 2, 4, 5, 11 and 12, wherein the SGSH variant comprises SEQ ID NO: 1 having an amino acid substitution at position 264.

54. The method of any one of claims 1, 2, 4, 5, 11 and 12, wherein the SGSH variant comprises SEQ ID NO: 1 having an asparagine (N)→glutamine (Q) substitution at position 264.

* * * * *

SEQUENCE LISTING

<160> NUMBER OF SEQ ID NOS: 3

<210> SEQ ID NO 1
<211> LENGTH: 502

-continued

```
<212> TYPE: PRT
<213> ORGANISM: Homo sapiens

<400> SEQUENCE: 1

Met Ser Cys Pro Val Pro Ala Cys Cys Ala Leu Leu Val Leu Gly
1               5                   10                  15

Leu Cys Arg Ala Arg Pro Arg Asn Ala Leu Leu Leu Ala Asp Asp
            20                  25                  30

Gly Gly Phe Glu Ser Gly Ala Tyr Asn Asn Ser Ala Ile Ala Thr Pro
        35                  40                  45

His Leu Asp Ala Leu Ala Arg Arg Ser Leu Leu Phe Arg Asn Ala Phe
    50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
130                 135                 140

Val Leu Gln Val Gly Arg Asn Ile Thr Arg Ile Lys Leu Leu Val Arg
145                 150                 155                 160

Lys Phe Leu Gln Thr Gln Asp Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
        275                 280                 285

Gly Thr Ala Glu Pro Leu Leu Val Ser Ser Pro Glu His Pro Lys Arg
    290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe
    370                 375                 380

Arg Leu Val His Asn Leu Asn Phe Lys Met Pro Phe Pro Ile Asp Gln
385                 390                 395                 400
```

Asp Phe Tyr Val Ser Pro Thr Phe Gln Asp Leu Leu Asn Arg Thr Thr
                405                 410                 415

Ala Gly Gln Pro Thr Gly Trp Tyr Lys Asp Leu Arg His Tyr Tyr Tyr
            420                 425                 430

Arg Ala Arg Trp Glu Leu Tyr Asp Arg Ser Arg Asp Pro His Glu Thr
                435                 440                 445

Gln Asn Leu Ala Thr Asp Pro Arg Phe Ala Gln Leu Leu Glu Met Leu
450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu
            500

<210> SEQ ID NO 2
<211> LENGTH: 306
<212> TYPE: DNA
<213> ORGANISM: Cytomegalovirus

<400> SEQUENCE: 2
gcgttacata acttacggta aatggcccgc ctggctgacc gcccaacgac cccgcccat      60 tgacgtcaat aatgacgtat gttcccatag taacgccaat agggactttc cattgacgtc     120
aatgggtgga gtatttacgg taaactgccc acttggcagt acatcaagtg tatcatatgc     180
caagtacgcc ccctattgac gtcaatgacg gtaaatggcc cgcctggcat tatgcccagt     240
acatgacctt atgggacttt cctacttggc agtacatcta cgtattagtc atcgctatta     300
ccatgg                                                                306

<210> SEQ ID NO 3
<211> LENGTH: 1672
<212> TYPE: DNA
<213> ORGANISM: Artificial Sequence
<220> FEATURE:
<223> OTHER INFORMATION: CAG promoter

<400> SEQUENCE: 3
atagcccata tatggagttc cgcgttacat aacttacggt aaatggcccg cctggctgac      60
cgcccaacga ccccgcccca ttgacgtcaa taatgacgta tgttcccata gtaacgccaa     120
tagggacttt ccattgacgt caatgggtgg agtatttacg gtaaactgcc cacttggcag     180
tacatcaagt gtatcatatg ccaagtacgc cccctattga cgtcaatgac ggtaaatggc     240
ccgcctggca ttatgcccag tacatgacct tatgggactt tcctacttgg cagtacatct     300
acgtattagt catcgctatt accatggtcg aggtgagccc cacgttctgc ttcactctcc     360
ccatctcccc cccctcccca ccccaatttt gtatttatt tattttttaa ttattttgtg     420
cagcgatggg gcggggggg ggggggggc gcgcgccagg cggggcgggg cggggcgagg     480
ggcggggcgg ggcgaggcgg agaggtgcgg cggcagccaa tcagagcggc gcgctccgaa     540
agtttccttt tatggcgagg cggcggcgg ggcggcccta taaaaagcga agcgcgcggc     600
gggcggggag tcgctgcgac gctgccttcg ccccgtgccc cgctccgccg ccgcctcgcg     660
ccgcccgccc cggctctgac tgaccgcgtt actcccacag gtgagcgggc gggacggccc     720
ttctcctccg gctgtaatt agcgcttggt ttaatgacgg cttgtttctt ttctgtggct     780
gcgtgaaagc cttgaggggc tccggagggc ccctttgtgc ggggggagcg gctcggggggg     840

```
tgcgtgcgtg tgtgtgtgcg tggggagcgc cgcgtgcggc tccgcgctgc ccggcggctg    900
tgagcgctgc gggcgcggcg cggggctttg tgcgctccgc agtgtgcgcg aggggagcgc    960
ggccgggggc ggtgcccgc ggtgcggggg gggctgcgag gggaacaaag gctgcgtgcg   1020
gggtgtgtgc gtgggggggt gagcaggggg tgtgggcgcg tcggtcgggc tgcaaccccc   1080
cctgcacccc cctccccgag ttgctgagca cggcccggct tcgggtgcgg ggctccgtac   1140
ggggcgtggc gcggggctcg ccgtgccggg cgggggggtgg cggcaggtgg gggtgccggg   1200
cggggcgggg ccgcctcggg ccggggaggg ctcggggggag gggcgcggcg gccccggag   1260 cgccggcggc tgtcgaggcg cggcgagccg cagccattgc cttttatggt aatcgtgcga   1320
gagggcgcag ggacttcctt tgtcccaaat ctgtgcggag ccgaaatctg ggaggcgccg   1380
ccgcaccccc tctagcgggc gcggggcgaa gcggtgcggc gccggcagga aggaaatggg   1440
cggggagggc cttcgtgcgt cgccgcgccg ccgtcccctt ctccctctcc agcctcgggg   1500
ctgtccgcgg ggggacggct gccttcgggg gggacggggc agggcggggt tcggcttctg   1560
gcgtgtgacc ggcggctcta gagcctctgc taaccatgtt catgccttct tcttttcct   1620 acagctcctg ggcaacgtgc tggttattgt gctgtctcat cattttggca aa           1672
```